US009725523B2

(12) United States Patent
Bower et al.

(10) Patent No.: US 9,725,523 B2
(45) Date of Patent: *Aug. 8, 2017

(54) MUTANT BACTERIAL STRAINS OF THE GENUS SPHINGOMONAS DEFICIENT IN PRODUCTION OF POLYHYDROXYBUTYRATE AND A PROCESS OF CLARIFICATION OF SPHINGANS AND COMPOSITIONS THEREOF

(71) Applicant: CP Kelco U.S., Inc., Atlanta, GA (US)

(72) Inventors: Stan Bower, La Jolla, CA (US); Ellen Burke, San Diego, CA (US); Nancy E. Harding, San Diego, CA (US); Yamini N. Patel, San Diego, CA (US); J. Carrie Schneider, San Diego, CA (US); Dagmar Meissner, San Diego, CA (US); Neil A. Morrison, San Diego, CA (US); Ralph Bezanson, Alpine, CA (US)

(73) Assignee: CP KELCO U.S., INC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/060,780

(22) Filed: Mar. 4, 2016

(65) Prior Publication Data

US 2016/0176990 A1 Jun. 23, 2016

Related U.S. Application Data

(60) Continuation of application No. 14/515,017, filed on Oct. 15, 2014, now Pat. No. 9,290,783, which is a division of application No. 12/893,322, filed on Sep. 29, 2010, now Pat. No. 8,865,241, which is a continuation of application No. 11/292,356, filed on Dec. 2, 2005, now Pat. No. 7,829,697, which is a division of application No. 09/798,642, filed on Mar. 2, 2001, now Pat. No. 7,887,866.

(60) Provisional application No. 60/186,433, filed on Mar. 2, 2000.

(51) Int. Cl.
| | |
|---|---|
| *C08B 37/00* | (2006.01) |
| *C12N 1/20* | (2006.01) |
| *C12P 7/62* | (2006.01) |
| *C12P 19/04* | (2006.01) |
| *A23L 29/269* | (2016.01) |
| *A23L 21/10* | (2016.01) |
| *A23L 21/15* | (2016.01) |

(52) U.S. Cl.
CPC .......... *C08B 37/006* (2013.01); *A23L 21/10* (2016.08); *A23L 21/15* (2016.08); *A23L 29/269* (2016.08); *C12N 1/20* (2013.01); *C12P 7/62* (2013.01); *C12P 19/04* (2013.01)

(58) Field of Classification Search
None
See application file for complete search history.

(56) References Cited

U.S. PATENT DOCUMENTS

| | | | | |
|---|---|---|---|---|
| 3,516,983 | A | * 6/1970 | Colegrove | .......... C08B 37/0033 |
| | | | | 435/104 |
| 4,010,071 | A | 3/1977 | Colegrove | |
| 4,416,990 | A | 11/1983 | Rinaudo et al. | |
| 4,618,582 | A | * 10/1986 | Engelskirchen | ........ C12P 19/06 |
| | | | | 435/104 |
| 4,647,470 | A | 3/1987 | Sanderson et al. | |
| 4,869,916 | A | 9/1989 | Clark et al. | |
| 5,175,278 | A | 12/1992 | Peik et al. | |
| 5,300,429 | A | 4/1994 | Baird et al. | |
| 5,315,003 | A | 5/1994 | Maruyama et al. | |
| 5,354,671 | A | 10/1994 | Pollock | |
| 5,595,892 | A | 1/1997 | Murofushi et al. | |
| 5,602,241 | A | 2/1997 | Maruyama et al. | |
| 5,744,428 | A | 4/1998 | Dreveton et al. | |
| 5,854,034 | A | 12/1998 | Pollock et al. | |

(Continued)

FOREIGN PATENT DOCUMENTS

| | | |
|---|---|---|
| EP | 0473222 | 3/1992 |
| EP | 0577326 | 1/1994 |

(Continued)

OTHER PUBLICATIONS

EMBL Online! Database, Accession No. D88825, Aug. 21, 1997, Fukui, T., "Aeromonas caviae phaC for PHA synthasem complete cds.".
Fukui, Toshiaki, et al., "Cloning and Analysis of the Poly(3-Hydroxybutyrate-co-3-Hydroxyhexanoate) Biosynthesis Genes of Aeromonas aviae," Journal of Bacteriology, Washington, D.C., vol. 179, No. 15, Aug. 1997, pp. 4821-3830.
Jansson, P.E., Lindberg, B. and Sandford, P.A. (1983) Structural studies of gellan gum, an extracellular polysaccharide elaborated by *Pseudomonas elodea*. Carbohydr. Res. 124:135-139.
O'Neill, M.A., Selvendran, R.R. and Morris, V.J. (1983) Structure of the acidic extracellular gelling polysaccharide produced by *Pseudomonas elodea*. Carbohydr. Res. 124:123-133.

(Continued)

Primary Examiner — Oluwatosin Ogunbiyi
(74) Attorney, Agent, or Firm — Eversheds Sutherland (US) LLP

(57) ABSTRACT

The invention relates to mutant strains of the genus *Sphingomonas* which have a mutation in at least one gene encoding a protein involved in polyhydroxybutyrate ("PHB") synthesis that allows the mutant strains to produce PHB-deficient Sphingans. The invention is also directed to a process for preparing a clarified Sphingan solution comprising heating aqueous Sphingan solution, in particular PHB-deficient Sphingan solution, to a clarification temperature of about 30° C. to about 70° C., and treating the solution with a clarification agent and enzymes. In addition, the invention is directed to a food or industrial product comprising a PHB-deficient and/or clarified Sphingan. One particular embodiment of the invention is directed to a clarified, PHB-deficient high-acyl gellan and the processes of making thereof.

16 Claims, 19 Drawing Sheets

(56) References Cited

U.S. PATENT DOCUMENTS

| | | | |
|---|---|---|---|
| 5,994,107 | A | 11/1999 | Murofushi et al. |
| 6,110,271 | A | 8/2000 | Skaggs et al. |
| 6,242,035 | B1 | 6/2001 | Clark et al. |
| 6,284,516 | B1 | 9/2001 | Pollock et al. |
| 7,868,167 | B2 | 1/2011 | Harding et al. |
| 8,198,064 | B2 | 6/2012 | Bower et al. |
| 8,231,921 | B2 | 7/2012 | Bezanson et al. |
| 8,278,438 | B2 | 10/2012 | Harding et al. |
| 2003/0100078 | A1 | 5/2003 | Harding et al. |

FOREIGN PATENT DOCUMENTS

| | | |
|---|---|---|
| EP | 0728841 A2 | 8/1996 |
| GB | 2065689 | 7/1981 |
| JP | 08154695 | 6/1996 |
| RO | 101634 | 7/1992 |
| WO | 96/36727 A1 | 11/1996 |

OTHER PUBLICATIONS

Kuo, M.S., Mort, A.J. and Dell A. (1986) Identification and location of L-glycerate, an unusual acyl substituent in gellan gum. Carbohydr. Res. 156:173-187.

Yamazaki, M., Thorne, LK., Mikolajckak, Mr., Armentrout, R.W., Pollock, T.J. (1986) Linkage of genes essential for a synthesis of a polysaccharide capsule in Sphinomonas strain S88, J. Bacteriol. 178:2676-2687.

Alexandra M.S. Carneiro De Melo, Claire A. Cassar and Roger J. Miles, "Trisodium Phosphate Increases Sensitivity of Gram-Negative Bacteria to Lysozyme and Nisin," Journal of Food Protection, vol. 61, No. 7, 1998, pp. 839-844.

H. Hague and A.D. Russell, "Cell Envelopes of Gram Negative Bacteria: Composition Response to Chelating Agents and Susceptibility of Whole Cells to Antibacterial Agents," J. Appl. Bact. 1976, 40, 89-99, Welsh School of Pharmacy, University of Wales Institute of Science and Technology, Cathays Park, Cardiff, Wales.

Vartak et al., 1995, "Glucose Metabolism in 'Sphingomonas Elodea': Pathway Engineering Via Construction of a Glucose-6-Phosphate Dehydrogenase Insertion Mutant," Microbiology, 141:2339-2350.

Tombolini et al., 1995, "Poly-beta-Hydroxybutyrate (PHB) Biosynthetic Genes in Rhizobium Meliloti 41," Microbiology, 141:2553-2559.

Umeda et al., 1998, "Cloning and Sequence Analysis of the Poly(3-Hydroxyalkanoic Acid)-Synthesis Genes of Pseudomonas Acidophila," Applied Biochemistry and Biotechnology, vol. 70-72, 341-352.

English Translation of Moriya et al. JP 08-1546975, 1996.

\* cited by examiner

TCTAGATTCGATCTCCTCTACTGGAATTCGGACGTCACCAACCTGCCGGCGACCTGGCAC
CTCAGCTACCTGACCGACCTCTACCGCGACAACAAGCTGATCGCGCCCGGCGCGCTCAGC
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯PHAC12
ATCGGCGGTACCCCGATCGACCTGTCGAAGGTAGAAACGCCGTCCTATATCCAGGCCGGG
CGCGAAGATCACATCGCACCGCCCCGCAGCGTCTGGAAGATGACGGAGCATTTCCGCGGG
CCGCACAAGTTCGTGCTGGCCGGTTCCGGCCATATCGCCGGCGTAATCAATCCGCCTTCG
GCAAAGAAATACCAATACTGGACCAATGCCGGGCCGGCCGAGTCGCTCGAATCCTTTGTC
GAAAACGCGACGGAACATGCCGGCAGCTGGTGGCCCCCTGGACTAGA       PHAC11

Fig. 2

*Pst*I   *phaC* gene
<u>CTGCAG</u>GACATGGCCAAGGGCCAGATGACGCAGACCGCCGCCGGCGCGTTCGAGCTCGGC
CGCAACCTGGCGATGACGCCGGGCAAGGTGGTGAAGCGCACGCCGCTGTACGAACTGATC
CAGTATTCGCCGACGACGGACACGGTGCTGGAAACGCCGCTGATCATCTTCCCGCCCTGG
ATCAACCGCTTCTACATTCTCGACCTGACGCCGGAGAAGAGCTTCATCCGCTGGGCGGTG
GCGCAGGGGATCACCGTGTTCGTCGTGTCGTGGCGCTCGGCCGATGCGAGCATGAAGGAC
GTGGTGTGGGACGATTATGTCGAGCGCGGCCAGATCGACGCGATCGACACCGTGCGCGAG
CTGCTCGGCGTGGAAAGCGTCCACACGATCGGCTATTGCGTGGCGGGCACCACGCTGGCG
GCGACGCTGGCGGTGCTCGCGGCGCGCGGGGAGGCGGCGAAGGTGGCGAGCGCGACCTTC
TTCACCGCCCAGGTCGACTTCACCGAGGCGGGCGACCTGCGCGTGTTCGTCGACGACGAC
CAGCTGGCGATGATCCGCAGCCTCGGCGCCGACGGGTTCCTCGACGGGCGCTACATGGCG
GCGACGTTCAACCTGCTGCGCGGGCGCGACCTGATCTGGAACTACGTCACCAACAACTAT
CTGATGGGGCAGGAATATGCGCCGTT<u>CGACCTGCTCCACTGGAA</u>CTCGGACGTCACCAAC
CTGCCGGCGRCCTGGCACCTCAGCTACCTGACCGACCTCTACCGCGACAACAAGCTGATC
GCGCC
               (<u>TCTAGA</u>)*Xba* I CGGCGCGCTCAGCATCGGCGGTACCCCGATCGACCTGTCGAAGGTAGAAACGCCGTCCTA
TATCCAGGCCGGGCGCGAAGATCACATCGCACCGCCCCGCAGCGTCTGGAAGATGACGGA
GCATTTCCGCGGGCCGCACAAGTTCGTGCTGGCCGGTTCCGGCCATATCGCCGGCGTAAT
CAATCCGCCTTCGGCAAAGAAATACCAATACTGGACCAATGCCGGGCCGGCC

*GAGTCGCTCGAATCCTTTGTCGAAAACGCGACGGAACATGCCGGAAGCTGGTGGCCGGAC*
*TGGg tGGACTGGTTGGTTGCGTTGAA*CAGTGCAAAGGTTGCGACGAAAGGTGCGCGGCTT
CCCGGCAGTGGAAACCTTTGTGCAATCGCCGACGCGCCCGGCGAATATGTTAGAATGCGC
TGACGGGAAGGCCGAATTTTCGCGGGTTTGACGATTTTTGTGCACTGCACAATGGCGCCT
TGCAAAATGGCCGTCGAGCCTTTATATGTTGCAGCGCAGCAATTGGCAGGGAAAGCTAGT
CAC<u>ATG</u>GCCAGCAAAGGACCTAAGACGACGGCCAAACCGGCGGCACGCGGTGCTACCAAG
CCCGCGACTCTGGCCGAAGCTGCCGCGGCGAAGCCGACGCCTGCACCCGCCCTTGCCGAG
ACGATCGTCCCGGCAGCGGCGCCGGTGCCGGCGCCTGCCGAAGCCGCTGCACCGCAGGAC
GTGAAGACCAACATCGAAGAGGCGATCACCGCCCGGTGGAAACGGCAGCCGCCGTCACC
GAGCAGGCGATCGAAGCCGCAGAGACCGTCGCGCCGGCGGTCACCACCAGCACCGCGAAG
GAAACGACTATCATGGCTACCACTTTCGAAAACGCGACTACCCAGGCCCAGACCGTTTTC
GCCGACCTGAATGAGCGCACCAAGGCCGCCGTCGAGAAGTCGACCAAGCTGGTCGAGGAA
GCCAACGAGTTCGCCAAGGGCAACATCGAAGCCCTGGTCGAATCGGGCCGCATCGCCGCC
AAGGGCTTCGAGAGCCTGGGCCAGGAAGCTGCCGATTACAGCCGCCGCTCGTTCGAGAGC
GCGACCGCCGCGCTGAAGGGCCTGTCGTCGGTCAAGTCGCCGACCGAATTCTTCAAG<u>CTG</u>
<u>CAG</u>
*Pst*I

Fig. 4 gatccacaccttgttctcgcgcgcccaggcgacgaggcgctcgtagaaggcgaggtccaccgtctccgcc
gtcgggttcgacggatagttgacgacgaggatcgacgggcgcggcacggtgaagttcattgcccgctcga
ggctttcgaaataggcgtcgtcgggcgtggtcggcaccgcgcggatcgtcgcgccggcgatgatgaagcc
gaaggtgtggatcgggtagctggggttgggcgcgagcaccacgtcgcccggcgcggtgatcgcggtggcg
aggctggcaaggccctccttcgagcccatcgtgacgacgacctcggtctcgggatcgagctcgacgcga
atcggcggccataataattggcctgggcgcggcgcaggcccggaatgcccttggactgcgaatagccgtg
cgcgtcgggcttcgcgcgccacttcgcacagtttctcgatcacatggtcgggcggcggcaggtccggattg
cccatgccgaggtcgataatgtcctctccgcccgcgcgtgccgctgcccgcatcgcgttcacttcggcga
tgacatagggaggcaagcgcttgatgcggtagaattcttcggacatttcctcgacttttcaagggttttga
cacgcgacacaaaattgtgtcgtgcgcgcgttctacgccataatcgcgcatccgggaatgacgcattgct
ccgcctgcgctaagccggggcgaaggagaggaccga atggccgatacgctcacgccgaccctgccccgactggaagacctgcagcattggacctgggtgctgggcc
gcgcgcagcagatgatgctggagcatgggctggacctgatggagcatgtgcccgccgcgcccccttcgg
catgctgctcgatccgacccggcaatgcgggcgagcgcggacctctgggcggacacgatgcagctgtgg
cagcgcttcctcgatcccgcccatgccgagccgttcgtcgaatcgcccgagcaggcgcgcgacaagcgct
tcaaggcgccgcaatggcgcgaggagccggtgttcgatttcctgcggcagagctatttcgtgatcgccga
ccacatgctcaggcaggtcgaggcgctcgagcatgtcgacgagcggcagcgggaccagatccgcttcgcc
accaagggcttcatcgacgcgatcagccccaccaacttcccgccaccaatccgcaggtgatcgagaaga
tcgtcgagaccaaggggaaagctgctcaagggcctgcagcatatgctgcaggacatggccaagggcca
gatgacgcagaccgccgccggtgcgttcgagctcggccgcaacctggcgatgacgcccggcaaggtggtg
aagcgcacccgctctacgaactgatccagtattcgccgaccaccgagaccgtgctggaaacgccgctga
tcatcttcccgccctggatcaaccgcttctacatcctcgacctgacgcccgagaaaagcttcatccgctg
ggcggtggagcaggggatcaccgtgttcgtcgtctcctggcgctcggccgatgcgagcatgaaggacgtg
gtgtgggacgattatgtcgagcgcggccagatcgacgcgatcgacacggtgcgcgcgctgctcggcgtcg
agagcgtccataccatcggctattgcgtggcgggcaccacgctggcggcgacgctggcggtgctcgccgc
gcgcgggcaggcggcgaaggtggcgagcgcgaccttcttcaccgcgcaggtcgatttcaccgaggcgggc
gacctgcgcgtgttcgtcgatgacgaccagctggcgatgatccgcagcctcagcgccgacggcttcctcg
acgggcgctacatggcggcgaccttcaacctgctgcgcggccgcgacctgatctggaactacgtcaccaa
caactatctgatggggcaggaatatgcgccgttcgacctgctccactggaactcggacgtcaccaacctg
ccggcgacctggcatctcagctacctgaccgacctgtaccgcgacaacaagctgatcgcgcccggcgcgc
tgcgcatcggcggcaccccggtcgacctttcgaaggtcgaaacgccgtcctacatccaggccggccgcga
agatcatatcgcgccgccgcaaagcgtctggaagatcaccgagcatttcgcggggcgcacaagttcgtg
ctggcgggttccgggcatatcgcaggtgtaataaacccccggcggcgaagaaataccaatactggacca
atacagggcctgccgagtcgctcgactcctttatcgaaacgcgacggaacatgcgggaagttggtggcc
ggattggctggattgggtccgtgcgctgaacggtgcaaaggttgcgacgagcggtgcgcgggtgccgggg
ggtggtaacctttgtgcagttgcggaagcgcccggcgactatgttagaatgcgctga caaagaggcagaatttcgtgggtttctggcgttttgtgcactgcacaatgatcgcttgcaaaagcagcg
ccaagtctttatatgctgcagtgcagcaatagccagggaaagctagtcacatggccagcaaaggacccaa
gacgacggccaaaccgccgcaaaatcagcggctcgcggtgctatcaagcccgcgattctggccgaagct
gccgcggcgacgccggcgtctgtacctcccgttgccgagacgatcgtcccggccgcggcgttggtgcctg
cgccggacgaagccgctgcaacgcaggaagtgacgactcacatcaaagacacggtcgacgttgcggcgga
aacggtaaaggccgtcgccgaacacgcgatcgaagccgcagagaccgtcgcgccggcggtcaccaccagc
accgcgaaggaaccgactatcatggccaccactttcgagaacgcgaccacccaggcccagactgttttcg
ccgacctcaacgagcgcaccaaggccgccgtcgaaaagtcgaccaagctggtcgaggaagccaacgagtt
cgccaagggcaacatcgaggcgctggtcgaatccggccgcatcgctgccaagggcttcgagacgctgggc
caggaagccgccgattacagccgtcgctcgttcgagaacgccacgaccacgctgaagagcctgtcgtcgg
tgaagtc

Fig. 10

MUTANT BACTERIAL STRAINS OF THE GENUS SPHINGOMONAS DEFICIENT IN PRODUCTION OF POLYHYDROXYBUTYRATE AND A PROCESS OF CLARIFICATION OF SPHINGANS AND COMPOSITIONS THEREOF

CROSS REFERENCES TO RELATED APPLICATIONS

This application is a continuation of U.S. application Ser. No. 14/515,017, filed Oct. 15, 2014, now U.S. Pat. No. 9,290,783, which is a divisional of U.S. application Ser. No. 12/893,322 filed Sep. 29, 2010, now U.S. Pat. No. 8,865,241, which is a continuation of U.S. application Ser. No. 11/292,356 filed Dec. 2, 2005, now U.S. Pat. No. 7,829,697, which is a divisional of U.S. application Ser. No. 09/798,642 filed Mar. 2, 2001, now U.S. Pat. No. 7,887,866, which claims the benefit of U.S. Provisional Patent Application No. 60/186,433, filed Mar. 2, 2000.

BACKGROUND OF THE INVENTION

Field of the Invention

The present invention relates to mutant bacterial strains of the genus *Sphingomonas* that are deficient in production of an internal storage polymer, polyhydroxybutyrate ("PHB") due to a null mutation, but produce normal quality of the capsular polysaccharides commonly referred to as Sphingans. The present invention also relates to a method of clarifying the Sphingans produced by a mutant strain of *Sphingomonas* that is deficient in the production of PHB. The present invention further relates to food or industrial products comprising PHB-deficient and/or clarified Sphingans.

Discussion of the Related Art

Sphingans are capsular polysaccharides secreted by bacteria of the genus *Sphingomonas*. Sphingans are structurally related, but not identical. Common members of the genus *Sphingomonas* and the Sphingans they produce include *Sphingomonas elodea*, ATCC 31461, which produces gellan (S-60); *Sphingomonas* sp. ATCC 31555, which produces welan (S-130); *Sphingomonas* sp. ATCC 31961, which produces rhamsan (S-194); *Sphingomonas* sp. ATCC 53159, which produces diutan (S-657); *Sphingomonas* sp. ATCC 31554, which produces an as yet unnamed polysaccharide (S-88); *Sphingomonas* sp. ATCC 31853, which produces an as yet unnamed polysaccharide (S-198); *Sphingomonas* sp. ATCC 21423, which produces an as yet unnamed polysaccharide (S-7); *Sphingomonas* sp. ATCC 53272, which produces an as yet unnamed polysaccharide (NW-11); *Sphingomonas* sp. FERM-BP2015 (previously *Alcaligenes latus* B-16), which produces alcalan (Biopolymer B-16) and the like. A description of the Sphingomonads and the polysaccharides they produce can be found in U.S. Pat. Nos. 4,377,636; 4,326,053; 4,326,052 and 4,385,123 (for ATCC 31461 and its S-60 polysaccharide); in U.S. Pat. No. 4,342,866 (for ATCC 31555 and S-130); in U.S. Pat. No. 4,401,760 (for ATCC 31961 and S-194); in U.S. Pat. No. 5,175,278 (for ATCC 53159 and S-657); in U.S. Pat. Nos. 4,331,440 and 4,535,153 (for ATCC 31554 and S-88); in U.S. Pat. No. 4,529,797 (for ATCC 31853 and S-198); in U.S. Pat. No. 3,960,832 (for ATCC 21423 and S-7); in U.S. Pat. No. 4,874,044 (for ATCC 53272 and NW-11); in U.S. Pat. No. 5,175,279 (for FERM BP-2015 and B-16), all of which are incorporated by reference herein.

Sphingan polysaccharides are structurally related by the primary structure of their backbone, which comprises the sugars D-glucose, D-glucuronic acid, and L-rhamnose (or L-mannose). For example, the primary structure of gellan, S-60, comprises the sugars D-glucose, D-glucuronic acid and L-rhamnose in a 2:1:1 molar ratio, which are linked together to form a tetrasaccharide repeat unit in the following order: glucose, glucuronic acid, glucose, rhamnose. In the native form, gellan is modified by acetyl and glyceryl substituents on the same glucose residue. On average, gellan has one glycerate substituent per tetrasaccharide repeat unit and one acetate substituent per every two tetrasaccharide repeat units. The primary structure of another Sphingan, diutan, S-657, differs from gellan in that it has an additional disaccharide side chain of L-rhamnose attached to one glucose residue, thus forming a hexapolysaccharide repeat unit. S-657 contains acetyl groups at position 2 and/or position 6 of the other glucose residue.

Sphingan polysaccharides, which are also referred to as gums, are primarily used to thicken or gel aqueous solutions and are frequently classified into two groups: thickeners and gelling agents. Typical thickeners include starches, guar gum, carboxymethylcellulose, alginate, methylcellulose, xanthan, gum karaya and gum tragacanth. Common gelling agents include gellan, gelatin, starch, alginate, pectin, carrageenan, agar and methylcellulose.

Gelling agents are used in the food industry in a variety of applications, including confectionary jellies, jams, dessert gels, icings, dairy products, beverages and the like. Additionally, gelling agents may be used as components of microbiological media. Gelling agents differ in the conditions under which they may be used and in the texture of the gels they form. These distinctive properties of gels have led to the exclusive use of certain gelling agents in particular products (e.g., starch in confectionary jellies; gelatin in dessert gels; agar in icings; and alginate in pimento strips).

Despite the use of certain gelling agents in particular products, disadvantages exist for conventional food formulations. For example, gelatin, which is frequently used in dessert gel formulations, is animal-sourced, requires refrigeration to set and is limited in application due to its instability under heat. Carrageenan, carrageenan and locust bean gum blends, and pectin, which are frequently used in dessert gel, confectionery and jam/jelly formulations, are generally limited to formulations that are brittle and inelastic in texture, suffer from poor storage stability and may be geographically restricted from use in some countries, such as Japan. Starch, which is frequently used in confection formulations, provides poor clarity and poor flavor release. Consequently, it would be desirable to develop a gelling agent for use in food formulations that is free from the problems associated with conventional gelling agents.

One particularly useful gelling agent is gellan (S-60), which is a capsular polysaccharide produced by the bacterium *Sphingomonas elodea*, ATCC 31461. Commercially, the gum is formed by inoculating a fermentation medium under aerobic conditions with *Sphingomonas elodea* bacteria. The fermentation medium contains a carbon source, phosphate, organic and inorganic nitrogen sources and appropriate trace elements. The fermentation is conducted under sterile conditions with strict control of aeration, agitation, temperature and pH. Upon completion of the fermentation, the viscous broth is pasteurized to kill viable cells prior to recovery of the gum. However, the optimal fermentation conditions for producing gellan also promote production of the internal storage polymer, polyhydroxybutyrate ("PHB"), which interferes with the ultimate clarification and recovery of gellan. During fermentation, PHB synthesis and gellan synthesis compete for the available carbon source, and PHB synthesis may compete with gellan synthesis.

Gellan displays different characteristics depending upon the method of recovery from the fermentation broth. Direct recovery from the fermentation broth yields gellan in its native or high-acyl form, which is modified by S. elodea with acetyl and glyceryl substituents on one glucose residue. Isolation of gellan in this native or high-acyl form yields a soft, flexible, elastic gel. Gellan may be deacylated by treatment with hot alkali, thereby providing gellan in its low acyl form. Isolation of gellan in this deacylated form yields a hard, firm, brittle gel, which has limited commercial applications. Blends of native and deacylated gellan produce gels of intermediate texture.

Certain applications require clear gellan. Currently, however, only deacylated gellan can be clarified. During the deacylation process, gellan is treated with alkali at high temperature, which removes the acyl substituents from the gellan and lyses the S. elodea cells. Solids and cell debris are then removed by filtration yielding a clear, non-acylated gellan. To date it has not been possible to clarify gellan in its native or high-acyl form via filtration due to the high set temperature (the temperature at which a gum forms a gel upon cooling) required and the capsular nature of the organism, which does not allow facile separation of gellan from the S. elodea cells. For applications requiring native gellan, S. elodea cells may be lysed chemically or enzymatically; however, the remaining PHB will be present in the final product and renders the resulting solutions turbid, rather than clear.

In addition to the use of gellan as a gelling agent, other Sphingan polysaccharides have also found useful commercial application. The S-657 polysaccharide imparts significant pseudoplasticity to polar solvents such as water, such that S-657 can act as a rheological modifier that is capable of particle suspension, friction reduction, emulsion and foam stabilization, filter cake disposition and filtration control. Consequently, S-657 has found industrial utility as a Rheological modifier in a variety of cementitious systems, as disclosed in U.S. Pat. No. 6,110,271, which is incorporated herein by reference.

In addition to impairing clarity, the PHB found in Sphingans affects the rheological properties of their gums. In particular, the PHB in S-657 gum affects the ability of the polysaccharide to modify rheology in porous medial flow environments such as oil fields, wherein rheology plays a significant role in well-bore drilling, completion and workover fluids. In addition, PHB residue in S-657 may cause damage during reservoir formation and may reduce the productivity of wells. The presence of PHB furthermore limits the applicability of S-657 gum in household and personal care products, in which appearance is critical to consumer acceptance.

Accordingly, attempts have been made to eliminate PHB production in Sphingans. One way to alleviate the problem of interfering PHB production in Sphingomonas species has been to chemically induce a random mutation into a strain that inhibits production of PHB, such as described in U.S. Pat. No. 5,300,429, which discloses LPG-2, a mutant strain of Sphingomonas elodea that inhibits the production of PHB, but remains capable of producing gellan. Sphingomonas elodea was formerly known as Pseudomonas elodea and refers to the same organism. The LPG-2 strain is on deposit with the American Type Culture Collection and designated ATCC 53967. While the LPG-2 strain produces gellan, its quality is inconsistent, presumably due to the additional mutation(s) which occur with chemical mutagenesis.

Genetic engineering is a more selective mutagenesis approach for generating null mutant strains of Sphingomonas deficient for production of PHB. Genetic engineering permits selective mutation or deletion of a gene within the PHB synthesis pathway, which in turn permits complete inhibition of PHB production without affecting the quality of gum production.

Consequently, it would be highly desirable to develop mutant strains of Sphingomonas that are deficient in their ability to synthesize PHB, while maximizing Sphingan production and, concomitantly, mitigating the requisite effort to remove PHB from Sphingans.

SUMMARY OF THE INVENTION

The invention relates to mutant strains of the genus Sphingomonas wherein at least one gene encoding a protein involved in polyhydroxybutyrate ("PHB") synthesis is selectively mutated or deleted such that the mutant strains produce Sphingans but not PHB.

Another embodiment of the invention is directed to isolated DNA sequences isolated from the DNA of multiple Sphingomonas species, i.e. from ATCC 31461 and 53159, that encodes the protein PHB synthase.

Another embodiment of the invention is directed to a process of preparing a PHB-deficient, clarified Sphingan comprising the steps of fermenting a mutant strain of the genus Sphingomonas and clarifying the PHB-deficient Sphingan from a fermentation broth.

Still another embodiment of the invention is directed to a process for preparing a clarified Sphingan solution comprising heating a Sphingan fermentation broth to a clarification temperature of about 30° C. to about 70° C., treating the Sphingan fermentation broth with a clarification agent and then treating the fermentation broth with enzymes. Yet another embodiment of the invention is directed to a process of preparing a clarified Sphingan solution comprising the steps of heating a Sphingan fermentation broth to a clarification temperature of about 30° C. to about 70° C., treating the fermentation broth with a chelating agent, treating the fermentation broth with a lysozyme enzyme, treating the fermentation broth with a caustic or oxidizing agent, and treating the fermentation broth with a protease enzyme.

Another embodiment of the invention is directed to mutant strains of Sphingomonas elodea that permit the preparation of a clarified, PHB-deficient, high-acyl (native) gellan with high gel strength.

Still another embodiment of the invention is directed to a food or industrial product comprising a PHB-deficient and/or clarified Sphingan.

BRIEF DESCRIPTION OF THE DRAWINGS

Figure 1A:
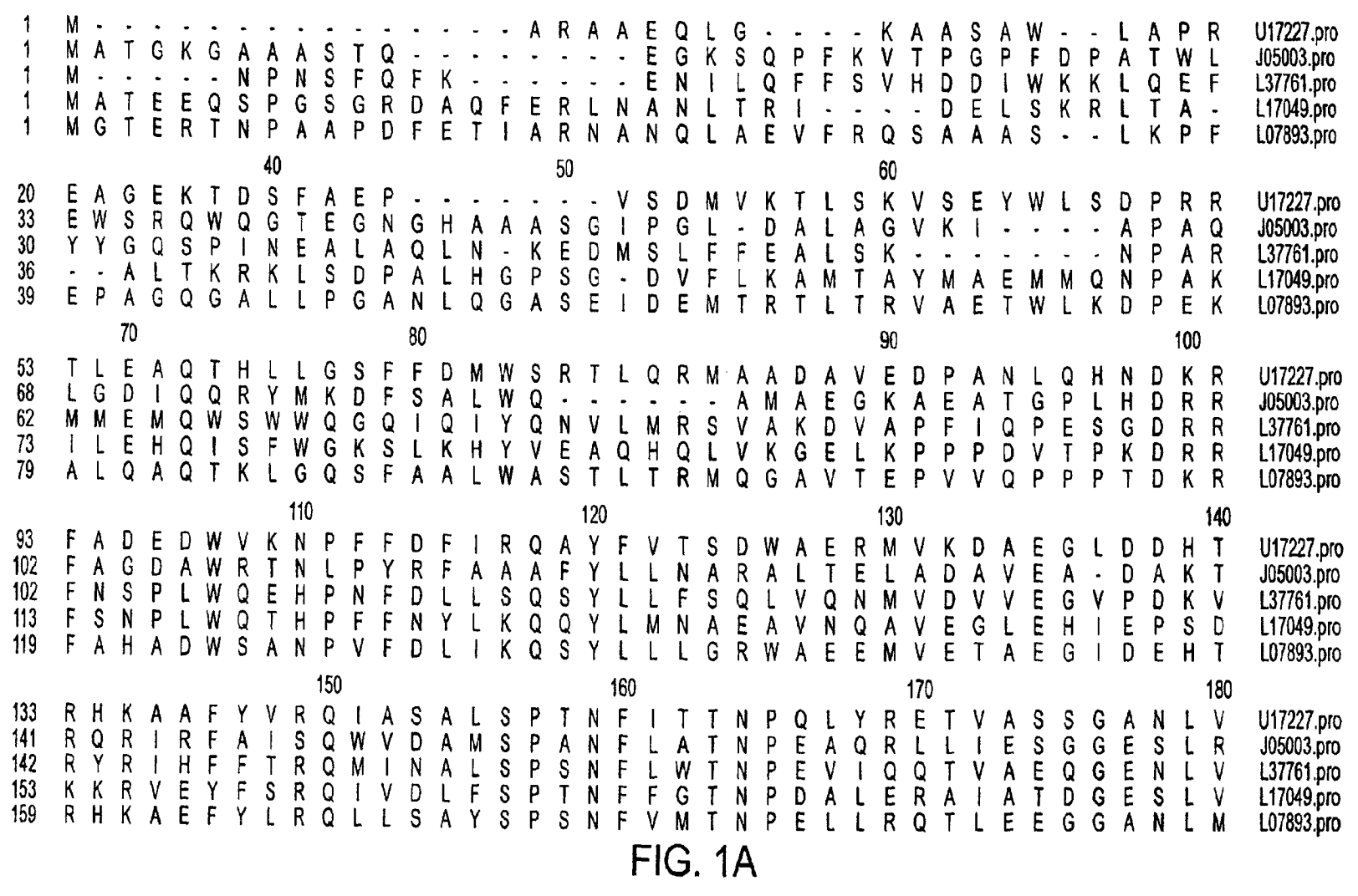
Figure 1B:
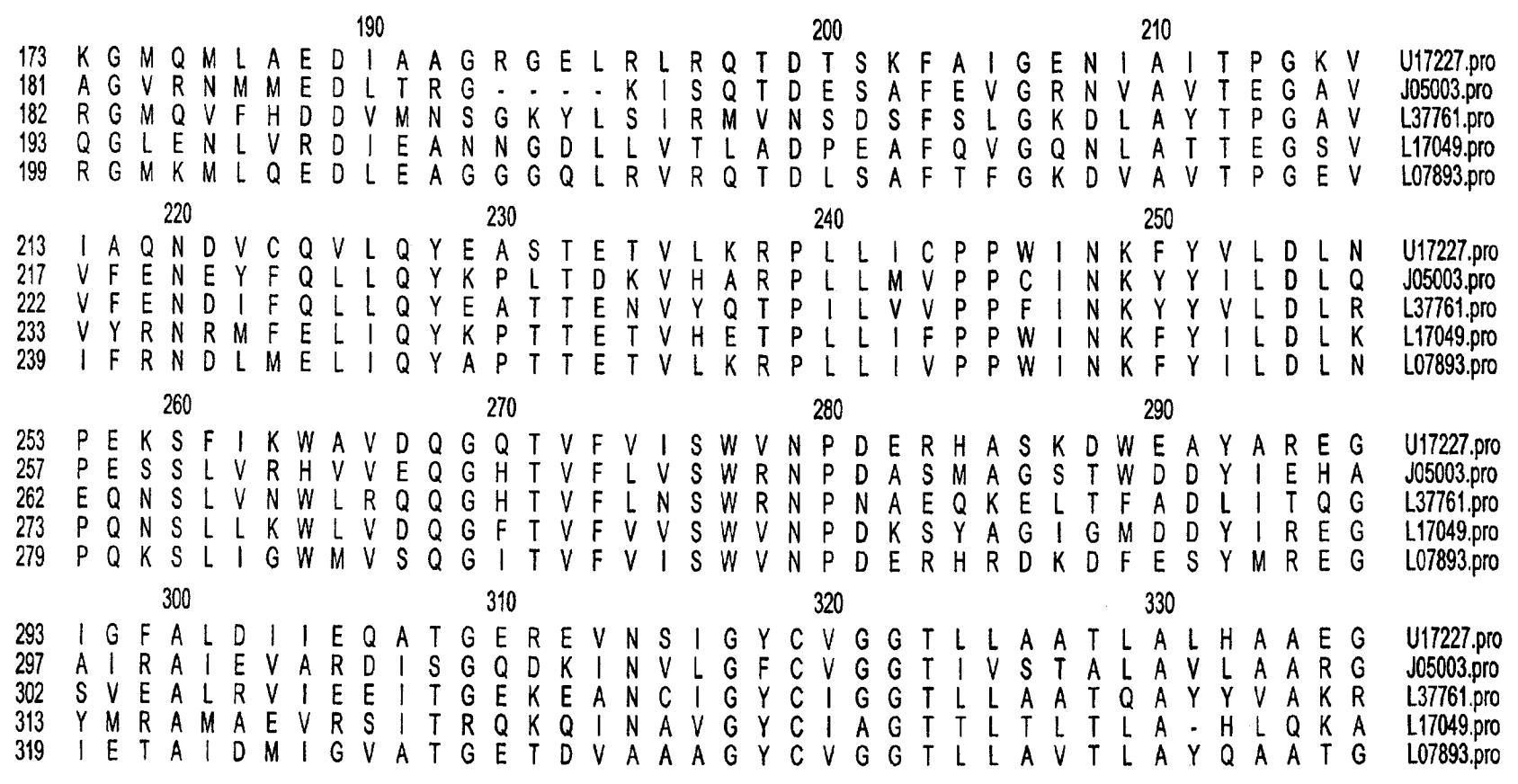
Figure 1C:
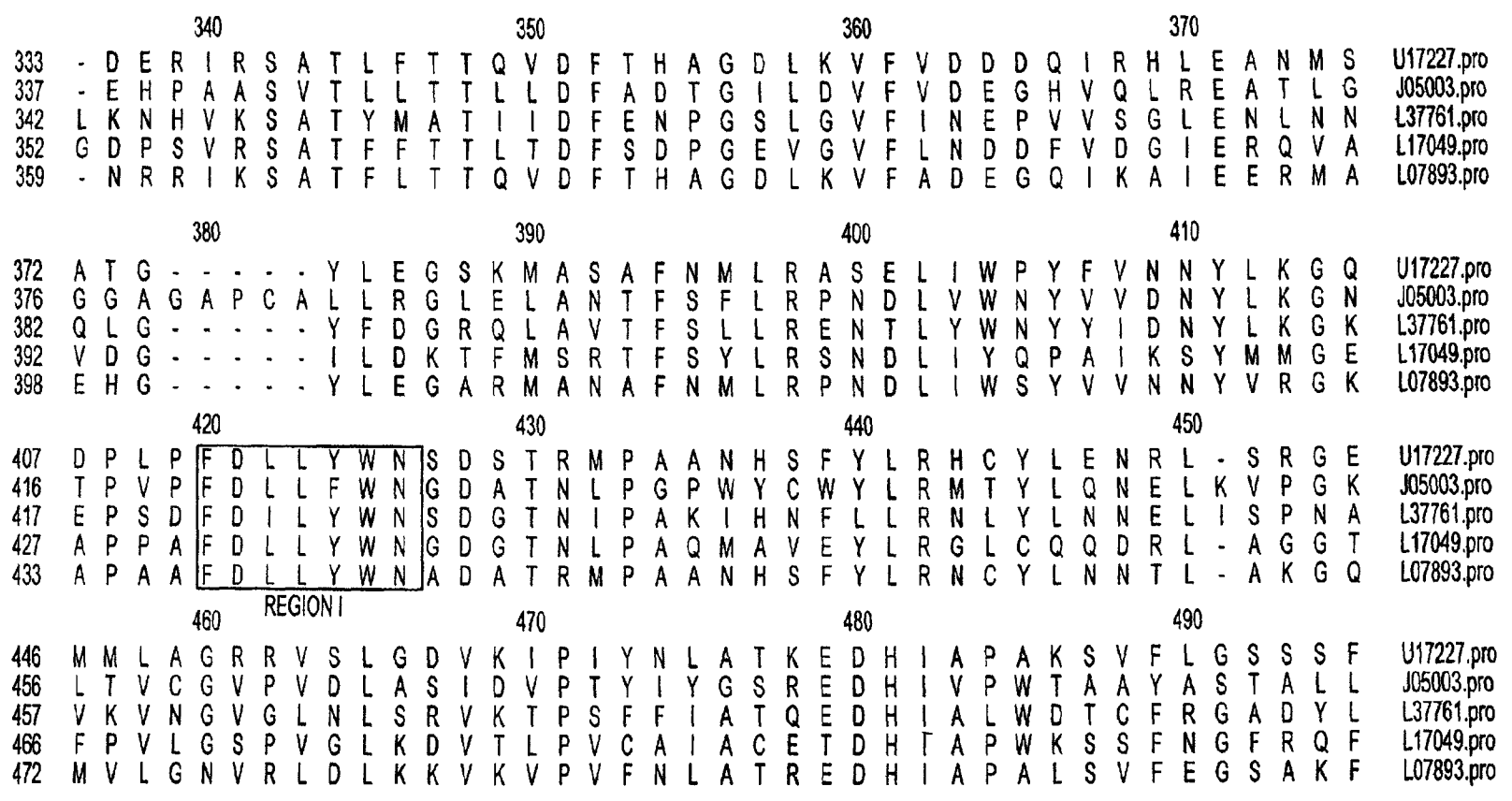
Figure 1D:
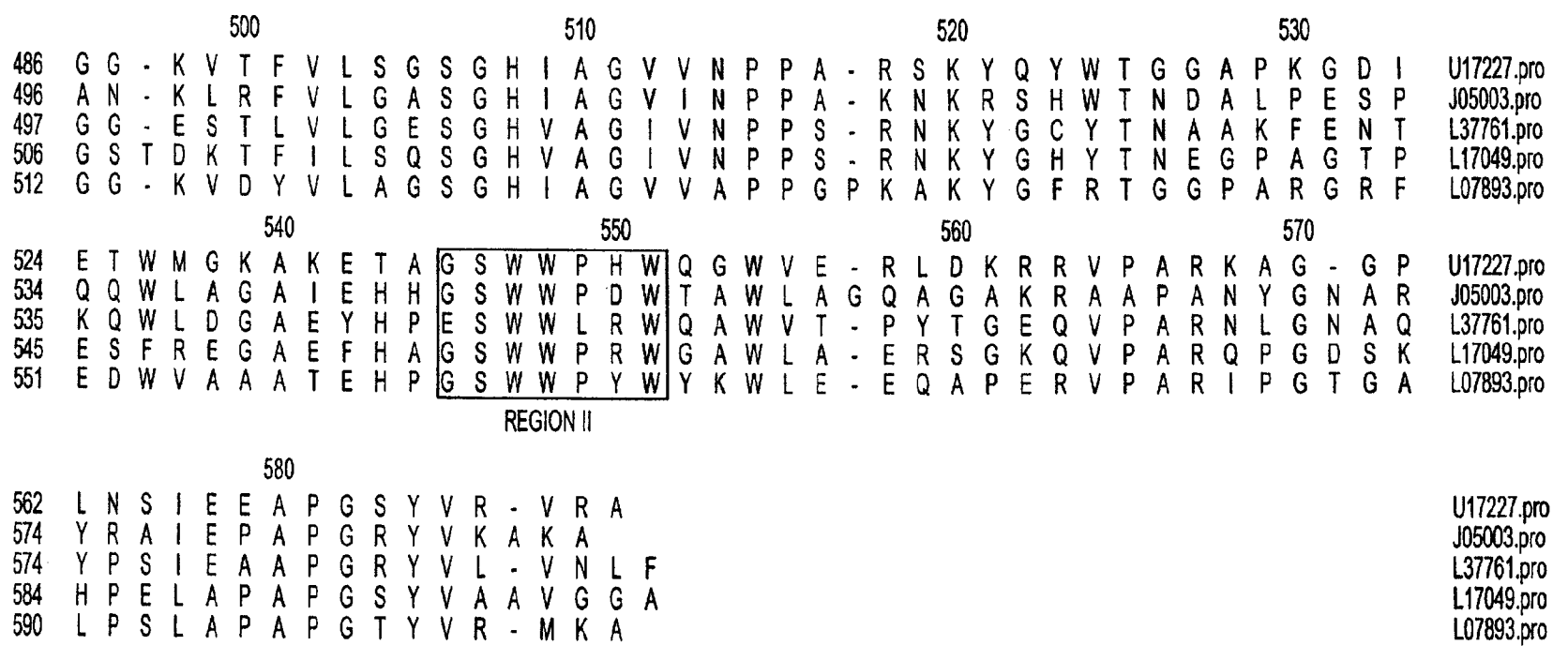

FIG. 1A-FIG. 1D depict sequential regions of PHB synthase protein sequences from Rhizobium meliloti (U17227) (SEQ. ID NO: 1), Alcaligenes eutrophus (J05003) (SEQ ID NO: 2), Acinetobacter sp. strain RA3849 (L37761) (SEQ ID NO: 3), Rhodobacter spaeroides (L17049) (SEQ ID NO: 4) and Methylobacterium extorguens (L07893) (SEQ ID NO: 5) aligned using the software DNA star MegAlign® by LaserGene (Madison, Wis.). Regions I and II were selected as conserved regions with moderate degeneracy and positioned to provide a polymerase chain reaction ("PCR") product of about 400 base pairs ("bp").

FIG. 2 shows the sequence of the 408 bp insert in plasmid pEB1 (SEQ ID NO: 6).

FIG. 4 depicts the sequence of the phaC region (SEQ ID NO: 7). Restriction enzyme sites for PstI (CTGCAG) are underlined. Primer binding sites are indicated by arrows. A portion of phaC gene extends from the first PstI site to the TGA stop codon (in bold). The bases that are deleted in the mutants are set out separately. The XbaI site (TCTAGA, double underlined) is substituted for the deleted region in the mutants, as described in the text.

FIG. 10 is the DNA sequence of the phaC gene and flanking regions of ATCC 53159 (SEQ ID NO: 13). Restriction enzyme sites for BamHI (ggatc), EcoRI (gaattc) and NotI (gcggccgc) are underlined and the overlap primer sites are double-underlined. Primer sites are indicated by arrows. The phaC gene is highlighted in bold.

DETAILED DESCRIPTION OF THE INVENTION

Figure 3:
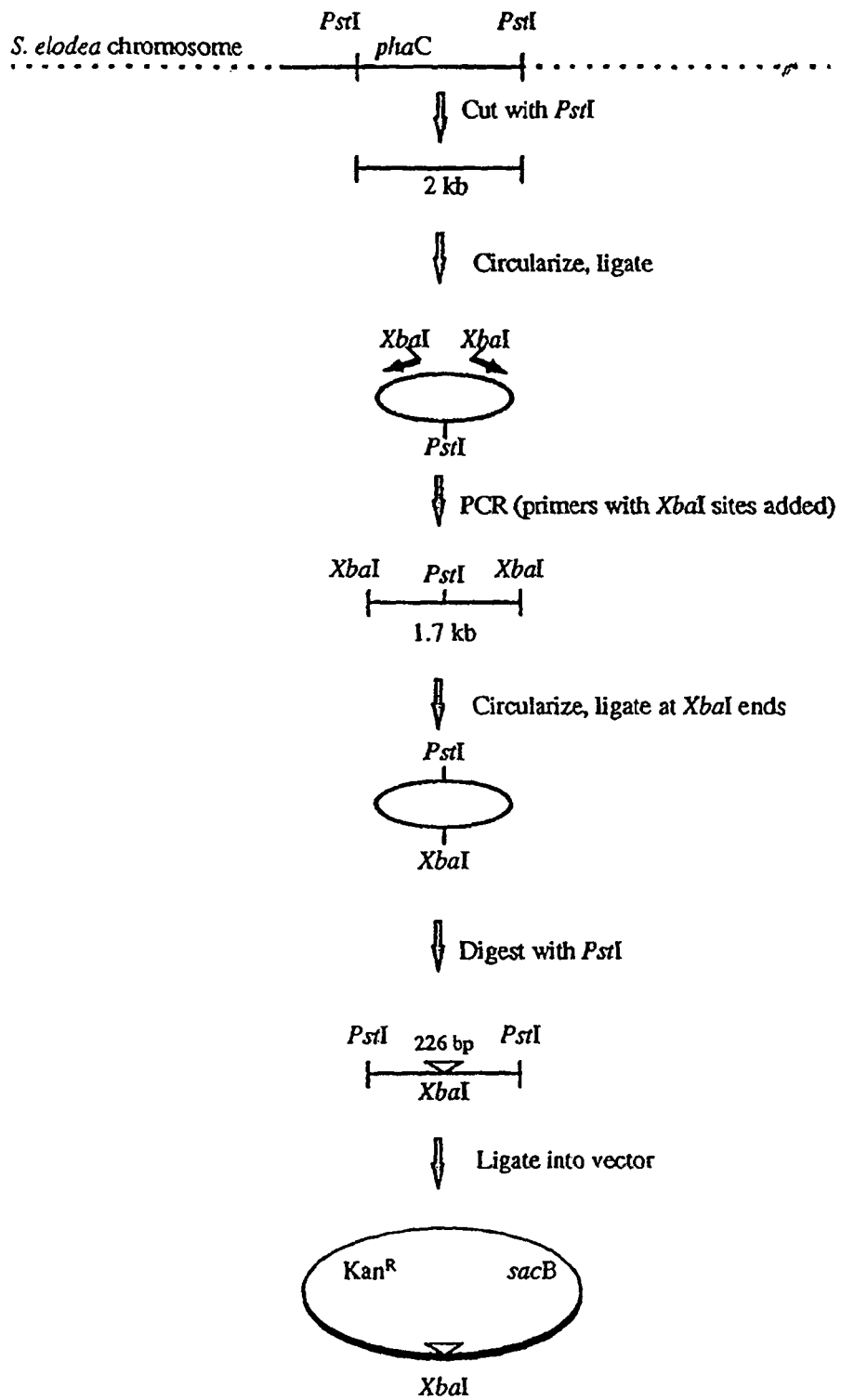
FIG. 3 is a schematic illustrating the steps used to clone and construct an internal deletion in the *Sphingomonas elodea* phaC gene.

The present invention relates to genetically engineered strains of the genus *Sphingomonas* deficient in their ability to synthesize the internal storage polymer polyhydroxybutyrate ("PHB") due to a null mutation which inactivates PHB synthesis. The PHB-deficient mutant *Sphingomonas* strains of this invention are capable of synthesizing commercially useful Sphingans which are free of PHB, as determined qualitatively by turbidimetric methods well known in the art (see example 4 below, and U.S. Pat. No. 5,300,429, the contents of which are incorporated by reference). PHB is a storage polymer that accumulates intracellularly in *Sphingomonas* under conditions of high carbon and low nitrogen, which are the same conditions that produce optimal levels of Sphingans.

PHB synthesis has been studied in a number of organisms, and at least three genes for PHB synthesis have been identified (Anderson, A. J. and E. A. Dawes, Microbiol. Rev 54: 450-72 (1990)). PHB is derived from acetyl coenzyme A (CoA) in three steps. The first step is catalyzed by 3-ketothiolase (phaA) and results in the formation of acetoacetyl CoA. In the second step, the enzyme acetoacetyl CoA reductase (phaB) converts acetoacetyl CoA to .beta.-hydroxybutyryl CoA, which is finally polymerized by PHB synthase (phaC) in the third step to form PHB. A mutation wherein at least one gene encoding a protein involved in polyhydroxybutyrate synthesis, i.e. phaA, phaB, or phaC, is selectively mutated or deleted may result in a PHB-deficient *Sphingomonas* strain.

For example, the *Sphingomonas* mutant strains described herein are the result of at least two mutations: (1) a deletion of or within the phaC gene encoding PHB synthase to block production of PHB, which had the unexpected result of diminishing Sphingan production; and (2) a spontaneous mutation to restore Sphingan production. The present invention also provides an optional preliminary mutation comprising a spontaneous mutation to increase the ability of *Sphingomonas* mutants to take up plasmid DNA, i.e. the S-60wtc mutation in *Sphingomonas elodea*.

Additionally, the present invention discloses a method of clarifying PHB-deficient gellan and other Sphingans produced by mutant *Sphingomonas* strains using chelating agents, caustic or oxidizing agents and enzymes for cell lysis and protein digestion. The present invention also discloses food or industrial products comprising PHB-deficient and/or clarified Sphingans.

To illustrate the details of the invention, the steps involved in the genetic engineering of *Sphingomonas elodea* and *Sphingomonas* sp. ATCC 53159 are described, however, as noted below, the invention is not limited to engineering *Sphingomonas elodea* and *Sphingomonas* sp. ATCC 53159 nor any particular gene encoding a protein involved in the synthesis of PHB.

An internal fragment of the *S. elodea* strain, ATCC 31461, phaC gene was obtained by PCR with degenerate primers designed from two conserved regions of phaC encoded proteins. The nucleotide sequence of this fragment, as shown in FIG. 2, was utilized to design primers for inverse PCR that allowed isolation of a larger portion of the phaC gene and 3' flanking sequence. Generally, the technique of inverse PCR clones the flanking regions of the nucleotides of interest in an orientation inverted to its natural orientation (See FIG. 3). The cloning process that arranged the inverted PCR fragments in their natural orientation resulted in a deletion of 232 base pairs ("bp"). Allelic exchange of this fragment for the chromosomal phaC gene eliminated PHB production in *S. elodea*. The internal 232 bp deletion had the unexpected effect of reducing gellan production. Spontaneous derivatives with restored gellan production were isolated from large scale growth of the mutant *S. elodea*. The PHB-deficient derivatives of the present invention contain no foreign DNA, a deletion of 232 bp from the native chromosome and an uncharacterized spontaneous mutation. The PDG-1 and PDG-3 strains are on deposit with the American Type Culture Collection and designated as ATCC No. PTA-4863 and ATCC No. PTA-4864, respectively both deposited on Dec. 20, 2002.

The particular molecular biology techniques, i.e. inverse PCR and deletion mutations, used to generate the *Sphingomonas* mutant for PHB production are not critical. It is within the knowledge of one of ordinary skill in the art to use conventional molecular biology techniques to generate Sphingomonas mutants. Other useful molecular biology techniques that may be used to mutate phaC-like genes in different Sphingomonas strains include, but are not limited to transposon mutagenesis, point mutations and insertion element mutations.

The phaC gene is only one gene in the PHB synthesis pathway; thus it is possible to generate Sphingomonas mutants with the desired phenotype, i.e., deficient in production of PHB, by selectively mutating or deleting other genes involved in the PHB synthesis pathway. Genes of interest that may be selectively mutated to yield the desired phenotype include, but are not limited to phaA (3-ketothiolase) and phaB (acetoacetyl CoA reductase).

Once the Sphingomonas mutants are generated, they are grown or fermented in an aqueous solution known as a fermentation broth into which the Sphingans are secreted as capsular polysaccharides. Following fermentation of the PHB-deficient Sphingomonas mutants, the Sphingans may be prepared by pasteurizing the broth and precipitating the Sphingan with an alcohol such as isopropanol, using techniques well-known in the art.

Preferably, following fermentation, the Sphingans can be clarified and isolated away from the suspended solids and cellular debris that are part of the fermentation broth milieu to yield PHB-deficient, clarified Sphingans. In addition, the clarification process of this invention may be applied to any Sphingan strain in addition to the above PHB-deficient Sphingans. As described herein, the clarification process comprises heating the fermentation broth and treating the fermentation broth with one or more chelating agents, one or more caustic or oxidizing agents, or a mixture thereof, followed by treatment with any lysozyme enzymes and/or any protease enzymes.

Specifically for gellan, the S. elodea mutant deficient in PHB production combined with the clarification process of this invention enables the production of clarified gellan in its high-acyl form. The gellan resulting from this mutant and process displays good clarity and high gel strength, which is useful for making dessert gels, confectionery, beverages and the like.

In one embodiment of this invention, hereinafter referred to as the "first protocol", aqueous solutions of Sphingans may be clarified by a process comprising treating the Sphingan solution with one or more optional surfactants, one or more chelating agents, one or more caustic or oxidizing agents, or a mixture thereof, and then treating with any lysozyme enzyme(s) and/or any protease enzyme(s).

In another embodiment of this invention, hereinafter referred to as the "second protocol" aqueous solutions of Sphingans may be clarified by a process comprising treating the Sphingan solution with one or more chelating agents, followed by any lysozyme enzyme(s), followed by one or more caustic or oxidizing agent(s), followed by any protease enzyme(s) or a mixture of protease enzymes.

In the first protocol, the process of this invention may be conducted in a stepwise manner, wherein the Sphingan solution is first treated with the chelating agent(s), optional surfactant(s), caustic or oxidizing agent(s) or a mixture thereof, and is then treated with any lysozyme enzyme(s) and/or any protease enzyme(s). In the second protocol, the stepwise process may be conducted wherein the Sphingan solution is first treated with the chelating agent(s), then any lysozyme enzyme(s), then the caustic or oxidizing agent(s) and then any protease enzyme(s), in that order.

Advantageously, the process for producing clarified Sphingan solutions described herein provides Sphingan solutions that may be used, if desired, after appropriate dilution, without any further chemical or mechanical treatment (except for pasteurization and precipitation). For some applications, Sphingans may be isolated from these clarified Sphingan broths by pasteurizing the broth, adjusting the broth to the desired pH and precipitating the Sphingan with an alcohol (i.e., isopropyl alcohol) according to conventional techniques.

Rehydration and dissolution of this Sphingan in water provides a substantially clear Sphingan solution. A substantially clear Sphingan solution (1% w/w), according to this invention, has a light transmittance greater than about 60%, preferably greater than 70%, and most preferably, greater than 80%. Light transmittance may be measured at any wavelength in the visible spectrum using conventional techniques and equipment (e.g., commercially available spectrophotometers). The light transmittance is typically measured at wavelengths of about 600 nm to about 650 nm. Light transmittance may be determined for several types of Sphingan solutions: untreated broth, partially treated broth (e.g., broth treated only with a chelating agent(s), a caustic or oxidizing agent(s), a chelating/caustic or chelating/oxidizing agent mixture, or a broth treated only with a lysozyme and/or protease enzyme), treated broth, or reconstituted Sphingan solutions. The substantially clear solutions described herein, having a light transmittance greater than about 60%, are aqueous solutions containing about 1% by weight of the Sphingan, isolated from a broth treated by the method according to this invention.

The Sphingan solutions that may be clarified using the process of this invention include the whole fermentation broth containing Sphingans obtained by fermentation of a Sphingan-producing microorganism in a nutrient medium, solutions obtained by addition of isolated Sphingans to aqueous media and partially purified Sphingan solutions. The aqueous solutions of Sphingans containing undesirable fermentation solids useful in the process of this invention may contain about 0.01% to about 10% Sphingan by weight of the total weight of the solution. Any aqueous solution containing any of the known Sphingans may be used in the practice of this invention.

The first step of either clarification process of this invention comprises heating a Sphingan solution to a clarification temperature by conventional techniques, such as temperature control in a jacketed tank, direct steam injection, or the like. Direct steam injection is preferred to minimize heating time. The clarification temperature ranges from about 30° C. to about 70° C. and, preferably, from about 50° C. to about 60° C. The length of time required to heat the Sphingan solution to the desired temperature may vary significantly depending upon the size and volume of the Sphingan solution to be treated. For example, whereas it may take only several minutes to increase the temperature of a small volume (e.g., 50 ml) of Sphingan solution from room temperature to about 60° C., it may take several hours to similarly increase the temperature of 40,000 liters of solution (e.g., as may be present in batch processing).

The next step of the process of this invention comprises treating an aqueous Sphingan solution with a clarification agent selected from at least one chelating agent, at least one caustic or oxidizing agent, or a mixture thereof, according to one of the two protocols. Alternatively, the addition of a clarification agent may be conducted simultaneously with heating the Sphingan broth to the clarification temperature described above.

In the first protocol, the next step is the addition of the chelating agent(s) to the Sphingan solution in the presence of caustic or oxidizing agent(s). Typically, the contact time for the chelating agent(s) and caustic/oxidizing agent(s) ranges from about 0.5 hours to about 2 hours each and, preferably, about 1 hour for the chelating agent(s) and from about 0.5 hours to about 1.0 hours for the caustic or oxidizing agent(s). Typically, the caustic or oxidizing agent(s) is added to the Sphingan solution at a concentration ranging from about 0 g/L to about 2 g/L and, preferably from about 0.5 g/L to about 1.5 g/L. Typically, the chelating agent(s) is added to the Sphingan solution at a concentration ranging from about 0 parts per million ("ppm"), to about 3000 ppm and, preferably, from about 1000 ppm to about 2000 ppm.

After treatment with the clarification agent in this first protocol, the Sphingan broth is subjected to an enzymatic treatment step, wherein the enzymes lysozyme and/or protease are added to the Sphingan broth either separately or simultaneously. Typically, the enzymes are contacted with the Sphingan broth for a time period ranging from at least about 0.5 hr to 8 hrs each, preferably at least 1 hr each, and most preferably at least 2 hrs each. The typical lysozyme concentration ranges from about 11,000 MCG units/L to about 44,000 MCG units/L, preferably, from about 20,000 MCG units/L to about 25,000 MCG units/L; the typical protease concentration ranges from about 65,000 Delft units/L to about 260,000 Delft units/L, preferably, from about 100,000 Delft units/L to about 150,000 Delft units/L. As used in this application, an "MCG unit" refers to a rate of lysis of *Micrococcus lysodeikticus* compared to a reference standard at pH 6.6 and 37° C. as described by Genencor International Inc.; similarly, the term "Delft unit" refers to a specific assay involving the rate of extinction of a case in solution provided by the vendor Genencor.

The enzymes used in the enzymatic treatment step degrade the solid cellular debris to soluble compounds, thus improving transmittance of the Sphingan solution and aiding in the clarification process. The protease enzymes suitable for use in this process may be acid, neutral or alkaline proteases from bacterial, fungal or plant sources. Exemplary acid protease enzymes useful in the process of this invention include, but are not limited to proteases produced by microorganisms of the genus *Aspergillus*, such as *A. niger*. The neutral protease enzymes useful in the process of this invention include, but are not limited to proteases such as *Bacillus amyloliquifaciens*. The alkaline protease enzymes useful in the process of this invention include, but are not limited to microorganisms of the genus *Bacillus*, such as *B. subtilis, B. licheniformis,* and *B. pumilis*, proteases elaborated by species of *Streptomyces*, such as *S. fradiae, S. griseus* and *S. rectus*, and proteases obtained from subtilisins, such as subtilisin Novo, subtilisin Carlsberg, including proteases such as subtilopeptidase A and subtilopeptidase B. The lysozymes suitable for use in this process include the Multifect® lysozyme from Genencor International Inc. (Rochester, N.Y.) or any lysozyme that may be obtained from a plant, animal or microbially-derived source. The source of any of the protease enzymes or lysozymes used in the present invention is not critical. These enzymes and the methods of obtaining them are well known in the art.

As described above in the first protocol, the enzymes comprising the enzyme treatment (treatment with lysozyme enzymes and/or protease enzymes) may be added simultaneously or separately. Simultaneous treatment refers to addition of the protease enzyme and lysozyme enzyme to the Sphingan solution in any order, over any period of time, provided that both enzymes are present in the Sphingan solution during the treatment. When added simultaneously, the enzyme treatment process of this invention is conducted under conditions such that both lysozyme enzymes and protease enzymes are active and provide the desired enzymatic function. The simultaneous enzyme treatment process of this embodiment may be conducted at a temperature of about 30° C. to about 70° C. at a pH of about 5 to about 9, and preferably about 6 to about 8. While the specific temperature and pH range of this embodiment may vary depending on the enzymes used, in this simultaneous embodiment, the process of the present invention is conducted at relatively mild temperatures and at nearly neutral conditions such that both the lysozyme enzyme and protease enzymes (acid, neutral or alkaline proteases) will demonstrate acceptable levels of activity to clarify the Sphingan solution.

Preferably, the enzyme treatment is conducted such that any lysozyme and/or protease enzymes are each separately added to the Sphingan solution. Most preferably, each enzyme is separately added to the Sphingan solution under its respective, optimal pH conditions, i.e. an acidic to neutral pH range for lysozyme (pH range of about 3 to about 7.5), and a neutral to basic pH range for protease (pH range of about 6.5 to about 9). The temperature and pH range at which different lysozyme and protease enzymes demonstrate optimal clarification activity may vary. Furthermore, if a choice must be made between lysozyme enzymes or protease enzymes for use in the enzyme treatment, then preferably the enzyme treatment comprises one or more protease enzyme(s).

In the second protocol, the chelating step is followed by enzymatic treatment with any lysozyme enzyme(s), which is followed by treatment with one or more caustic or oxidizing agent(s), followed by enzymatic treatment with any protease enzyme(s). As illustrated above, the enzymatic treatment is bifurcated between lysozyme enzyme(s) and protease enzyme(s). This alternative sequence allows any lysozyme enzyme(s) to act under its preferred neutral to acidic pH conditions, and allows any protease enzyme(s) to act under its preferred neutral to basic pH conditions. The same lysozyme and protease enzymes, and chelating, surfactant and caustic or oxidizing agents, may be used in practicing the second protocol as described above in the first protocol.

Agitation of the Sphingan solution is not essential, although where feasible the Sphingan solution is stirred or agitated mildly or periodically to avoid undue settling of the solids and promote contact with the enzymes.

Chelating agents that are suitable for use in the process of this invention are compounds or compositions that are capable of sequestering multivalent metal ions (e.g., $Mg^{+2}$, $Ca^{+2}$, etc.) in the Sphingan solution by forming poly-dentate complexes with the metal ions, forming a precipitate with the metal ions or adsorbing the metal ions. Preferably, the chelating agents are water or water-alcohol soluble compounds or compositions and are alkali metal or alkaline earth salts of organic and/or inorganic acids or organic/inorganic acid salts of basic (amine-containing) organic compounds, as well as the organic and/or inorganic acids or the basic compounds themselves. Other chelating agents useful in the process of this invention are cationic ion exchange resins and carbonic acid and carbonic acid salts. Salt compounds and compositions that are particularly useful in the process of this invention include the salts of ethylenediamine tetraacetic acid, phosphoric acid, metaphosphoric acid, carbonic acid, citric acid, tartaric acid, gluconic acid, glutamic acid, pyrophosphoric acid, polyphosphoric acid, metaphosphoric acids, saccharic acid, ethyleneglycol-bis-(beta-aminoethyl ether)-N,N,N',N'-tetraacetic acid (EGTA), ethylenediamine, 2,3-diaminobutane, 1,2-diaminocyclohexane, triaminotriethylamine and the like. Useful salts may include the mono-, di-, tri- and/or tetra-metal salts of the above acids and the mono-, di- or tri-acid salts of the above bases, as appropriate. Preferably, the chelating agents used in the process of this invention include salts of ethylenediamine tetraacetic acid, citric acid, phosphoric acid, pyrophosphoric acid, polyphosphoric acid, carbonic acid, metaphosphoric acid, and ethylenediamine. Examples of useful chelating agents include, but are not limited to, disodium ethylenediamine tetraacetate, dipotassium ethylenediamine tetraacetate, tetrasodium ethylenediamine tetraacetate, tetrapotassium ethylenediamine tetraacetate, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, ethylenediamine dihydroiodide and the like. More preferably, sodium hexametaphosphate is used as the chelating agent.

As described in the above protocols, surfactants may optionally be used in conjunction with the caustic, oxidizing and chelating agents in order to further improve transmittance in the final gellan product. Surfactants that are suitable for use in the process of this invention are compounds or compositions that are capable of forming aqueous emulsions in the presence of hydrophilic and hydrophobic substances (solids or liquids). Preferably, the surfactants are water or water-alcohol soluble compounds or compositions. Examples of useful surfactants include, but are not limited to SDS, polyoxyethylenesorbitan monooleate (Tween 80® by ICI Americas, Inc., Bridgewater, N.J.) but are not limited to SDS, lecithin, monoglycerides, tartaric esters of monoglycerides, phosphated monoglycerides (e.g., as the monosodium salt), lactylated monoglycerides, acetylated monoglycerides, succinylated monoglycerides, ethoxylated monoglycerides, sorbitan esters, polysorbates, polyglycerol esters, sucrose esters, sodium stearoyl lactylate, propylene glycol esters and the like.

The optional surfactants are added to the Sphingan broth at any time during treatment with the chelating agent(s), caustic or oxidizing agent(s), for a contact time ranging from about 0.5 hours to about 8 hours each and, preferably, about 2 hours. Typically, the surfactants are added to the Sphingan solution at a concentration ranging from about 0.0 g/L to about 3.0 g/L and, preferably from about 0.1 g/L to about 1.0 g/L. Typically, the surfactant(s) is added to the Sphingan solution at a concentration ranging from about 0 parts per million ("ppm"), to about 3000 ppm and, preferably, from about 300 ppm to about 1000 ppm.

Caustic agents that are suitable for use in the process of this invention include, but are not limited to, potassium hydroxide, sodium hydroxide, trisodium phosphate and the like. Potassium hydroxide is the preferred caustic agent. Alternatively, oxidizing agents may be used in lieu of caustic agents. Oxidizing agents that may be used in the clarification process of the present invention include sodium hypochlorite or other hypochlorite salts, chloride dioxide, hydrogen peroxide, peracetic acid, ozone, and other oxidizing agents well known in the art. In the present invention, the preferred oxidizing agent is sodium hypochlorite.

It should be noted that the degree of clarification effected by treatment of the Sphingan solution with chelating agent(s), surfactant(s), caustic or oxidizing agent(s) or mixture thereof may affect the enzyme concentrations or the time required to complete the subsequent enzyme treatment. For example, increasing the amount of the chelating agent (s), surfactant(s), caustic or oxidizing agent(s) or a mixture thereof used in this process may decrease the amount of enzymes used and/or the time required to effect clarification of a Sphingan solution. Adjustment and balancing of the concentration and length of treatment time of the chelating agent(s), surfactant(s), caustic or oxidizing agent(s) or mixture thereof and/or with the concentration and length of treatment time of the lysozyme and/or protease to obtain Sphingan solutions is preferable for optimizing production of the PHB-deficient, clarified Sphingans described herein.

The PHB-deficient and/or clarified Sphingans described herein may be used in a variety of food or industrial applications. For example, a PHB-deficient and/or clarified Sphingan such as native (high-acyl) gellan may be used to improve the taste, texture, stability and appearance of food products such as dessert gels, confections, jams and jellies, beverages, films, coatings and the like. As an additional example, a PHB-deficient and/or clarified Sphingan such as S-657 may find improved effectiveness as a rheological modifier in industrial applications such as oil-field drilling or cementitious systems. Other PHB-deficient and/or clarified Sphingans of the present invention will also find a greater range of application in both food products and industry.

The following examples provide illustrations of the present invention and should not be misconstrued to limit in any way the scope of the present invention.

Example 1

Generation of a *Sphingomonas elodea* phaC Fragment

To identify highly conserved regions of the PHB synthase gene, PHB synthase sequences from diverse organisms were retrieved from the National Center for Biotechnology Information ("NCBI") Gene Bank. Sequences from *Rhizobium meliloti* (gb: U17227) (SEQ ID NO: 1), *Rhodobacter spaeroides* (gb: L17049) (SEQ ID NO: 4), *Methylobacterium extorquens* (gb: 07893) (SEQ ID NO: 5), *Alcaligenes eutrophus* (gb: J05003) (SEQ ID NO: 2) and *Acinetobacter* sp. strain RA3849 (gb: L37761) (SEQ ID NO: 3) were selected and studied. The protein sequences of the selected PHB synthase genes were aligned as displayed in FIG. 1. Among the conserved regions, Region I (*R. meliloti* codons 411-417) and Region II (*R. meliloti* codons 535-541) were selected to provide a PCR product of about 408 bp based on their position and relatively low degree of degeneracy.

Degenerate PCR primers were designed to amplify the sequence between Region I and Region II based on the conserved protein sequences and the apparent codon preference of *Sphingomonas elodea*, ATCC 31461. The codon preference was inferred from the codon usage in five genes from the region encoding exopolysaccharide biosynthetic enzymes in *S. elodea*, ATCC 31461, sequenced by Dr. Luis Ielpi (unpublished) and from the complete exopolysaccharide biosynthetic enzyme gene cluster from the closely related *Sphingomonas* ATCC 31554, which produces S-88 gum (Yamazaki, et al., J. Bacteriol. 178: 2676-2687 (1996)).

The N-terminal primer, designated PHADG5 (SEQ ID NO: 9), comprised a 5'-AGTT clamp region, a TCTAGA XbaI site, and a TTC GAY CTS CTS TAY TGG AAY3' degenerate hybridizing region targeting Region I. The C-terminal primer, designated PHADG7 (SEQ ID NO: 10), comprised a 5'-GTAT clamp, a ACTAGT SpeI site, and a CCA III SGG CCA CCA GCT GCC degenerate region targeting Region II. In SEQ ID NO: 10, "I" refers to inosine, a nucleotide that is compatible with any other base, that is, A, C, T or G.

Primers PHADG5 (SEQ ID NO: 9) and PHADG7 (SEQ ID NO: 10) were utilized in a PCR reaction with chromosomal DNA from a non-mucoid strain, Gps31, serving as the template. Gps31 is a non-gellan producing mutant of S-60. Taq polymerase with the Taq Start® Antibody by Clontech Laboratories, Inc. (Palo Alto, Calif.) provided a hot start for PCR with 2.5 mM each dNTP, 4 mM $MgCl_2$ and 50 pmol each primer in a reaction volume of 100 .mu.l. The temperature program was 5 minutes 96° C., 30 cycles of 1 min 96° C., 1 min 58° C., 1 min 72° C., and 5 min 72° C. before stopping the reaction by chilling to 4° C. The PCR reaction resulted in a single band at the expected 416 bp size (408 bp plus clamps). Following digestion with XbaI and SpeI, the fragment was cloned into an XbaI digested, calf intestinal alkaline phosphatase ("CIAP") treated pUC19 vector to yield plasmid pEB1. The DNA sequence of the 408 bp insert (SEQ ID NO: 6) from both strands is illustrated in FIG. 2. The fragment contained restriction sites for EcoRI, KpnI and PvuII. An alignment of the translated cloned fragment with other PHB synthase proteins demonstrated that a PHB synthase had been cloned.

Example 2

Construction of phaC Deletion by Inverse PCR

Southern hybridization was used to determine an appropriate restriction enzyme that would provide a larger fragment of the *Sphingomonas* S-60 phaC gene that was still not too large for facile recovery by inverse PCR. Chromosomal DNA was isolated from Gps31 according to the method described in the QIAGEN® (Valencia, Calif.) DNA purification kit. A Southern analysis using a probe generated from the 408 bp insert (SEQ ID NO: 6) cloned in pEB1 demonstrated that in a PstI digest of *S. elodea* DNA, the 408 bp phaC fragment (SEQ ID NO: 6) resided on a fragment of about 2 kb.

The sequence of the 408 bp *Sphingomonas* S-60 phaC fragment (SEQ ID NO: 6) was used to select outward reading PCR primers, as illustrated in FIG. 2. Primer PHAC12 (SEQ ID NO: 11) reads toward the N-terminal end of the phaC encoded protein with a clamp 5'GTTC, an XbaI site TCTAGA, and hybridizing region. Primer PHAC11 (SEQ ID NO: 12) reads toward the C-terminal end of the phaC encoded protein with a clamp 5'GTTC, an XbaI site TCTAGA and hybridizing region. *S. elodea* chromosomal DNA was digested with PstI and 0.5 ug of DNA was ligated in a 200 ul volume to allow circularization. A KpnI digest to generate a linear DNA molecule was used as a template in an inverse PCR reaction to generate a 1.7 kb fragment of regions flanking the 408 bp phaC fragment (SEQ ID NO: 6), as depicted in FIG. 3.

The 1.7 kb fragment comprises the two flanking regions ligated in an orientation inverted relative to the native orientation at their PstI ends. Cleavage at the PstI site indicated that the flanking regions were of similar sizes, 850 bp and 980 bp. To reorient the fragment into its native orientation and, simultaneously, generate a fragment with most of the original 408 bp clone deleted, the 1.7 kb fragment was digested with XbaI, ligated to itself under dilute conditions to allow circularization and then digested with PstI. The resulting fragment was cloned into PstI-digested, CIAP-treated pUC19 and designated pEB4.

Example 3

Sequencing the phaC Clone

The 1.7 kb insert in pEB4 was sequenced and combined with the sequence of the 408 bp fragment (SEQ ID NO: 6). The combined 1920 bp DNA sequence (SEQ ID NO: 7) is depicted in FIG. 4. Part of this sequence, from the PstI site to the TGA stop codon (bases 1-1200) encodes a protein (SEQ ID NO: 8) which is homologous to the carboxy two-thirds of other phaC genes. Sequence alignment confirmed that the proper gene was cloned.

The phaC clone had a 232 bp deletion within the 408 bp segment and an insertion of 6 bp, TCTAGA, corresponding to the XbaI site. The deletion and insertion caused a frameshift mutation that altered the carboxy terminus and introduced a new termination codon at base pair 1102.

Example 4

Figure 5:
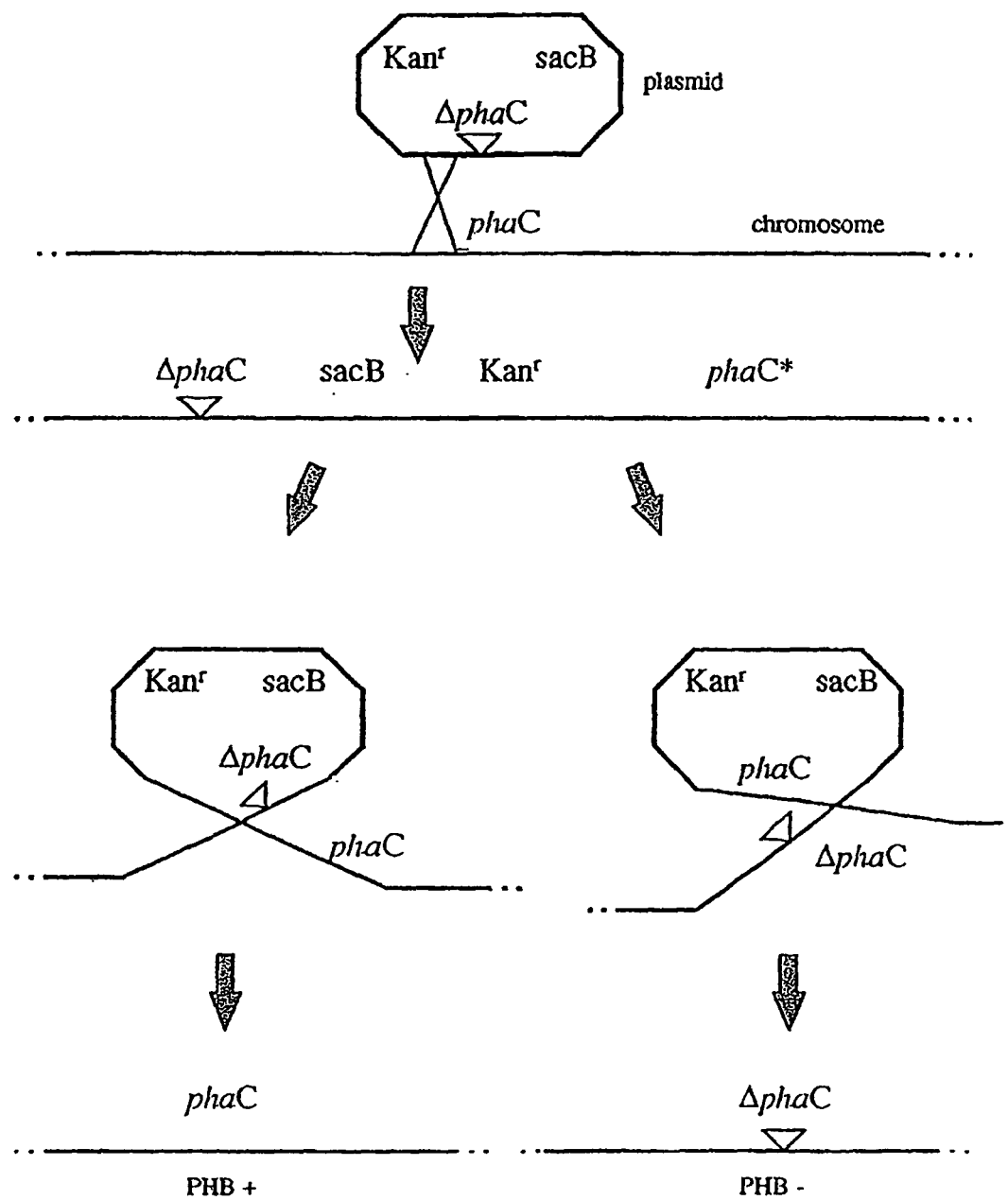
FIG. 5 is a schematic diagram of homologous recombination of mutated phaC gene into the *Sphingomonas elodea* chromosome and excision of the integrated vector leaving either an intact or mutated phaC gene in the chromosome.

Construction of an Integration Vector and Transfer to *Sphingomonas* by Homologous Recombination To transfer the phaC deletion mutation into *Sphingomonas elodea*, a "suicide" plasmid was used, which is capable of replication in a host suitable for plasmid construction, for example, *E. coli*, but incapable of replication in *Sphingomonas*. Selection in *Sphingomonas* for the antibiotic resistance encoded by the plasmid identifies those colonies in which the plasmid has integrated into the chromosome as a result of homologous recombination. Selection for the loss of antibiotic resistance identifies those colonies in which the duplicated region has recombined out, which may result in retention of the mutation (that is, the deletion) or wild-type genes, which is depicted diagrammatically in FIG. 5. Differentiation between clones with the deletion versus clones with the wild-type DNA may be determined by phenotypic expression (PHB synthesis). To measure phenotypic expression of PHB, a qualitative turbidimetric assay was used: an aliquot of broth, about 1 ml, was added to 9 volumes of Clorox® (Clorox Co., Oakland, Calif.) and incubated at 37° C. for at least 4 hours or overnight. Appearance of a white precipitate is indicative of the presence of PHB.

To facilitate detection of second crossover recombination events, a positive selection system was adapted for *S. elodea*. The *Bacillus subtilis* gene, sacB, which encodes a levansucrase, may be transferred into gram-negative bacteria (Kamoun. S. et al., Mol. Microbiol. 6:809-816 (1992); Gay, P. et al., J. Bacteriol. 164:918-921 (1985)). Growing these bacteria in sucrose promotes synthesis of levan, which is toxic to the bacteria. Consequently, if the sacB gene is present on a vector, growth in sucrose may be used to identify those isolates that have lost the vector.

Figure 6:
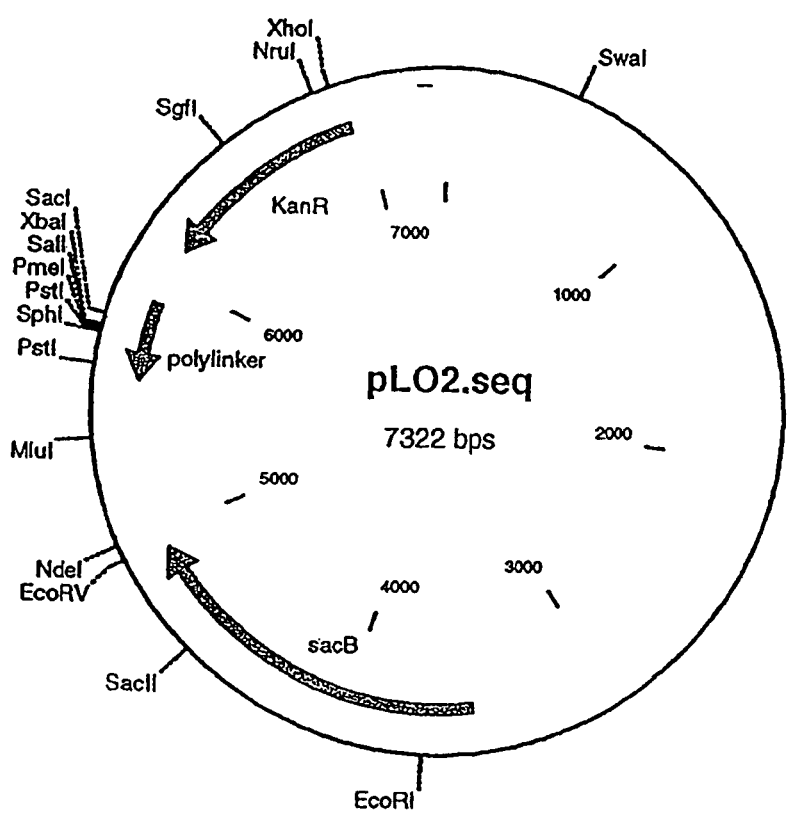
FIG. 6 is an illustration of the plasmid pLO2.

The pLO2 plasmid was obtained from Steven Slater at Cereon, Monsanto. The pLO2 plasmid contains the sacB gene on a vector with kanamycin resistance, the ColEI origin of replication and the RP4 origin of transfer as illustrated in FIG. 6 (Lenz, O. et al., J. Bacteriol. 176:4385-4393 (1994)). The pLO2 plasmid may be used to transfer genes through the natural process of conjugation. The plasmid can replicate in *E. coli*, but not *Sphingomonas*, and contains a site for mobilization of the plasmid but does not contain transfer functions. That is, the pLO2 plasmid is mobilizable but not self-transmissable. The genes for conjugal transfer function are supplied on a second plasmid and function in trans. While this example uses the pLO2 plasmid, its use is not critical. One of ordinary skill in the art would know how to design and engineer a suitable alternative plasmid and transfer it into *Sphingomonas* using conventional techniques, such as electroporation, transformation and the like. Similarly, use of kanamycin as a selectable marker is not critical. One of ordinary skill in the art would know how to choose an appropriate alternative selectable marker.

The 1.7 kb PstI fragment containing the phaC deletion was ligated into PstI-digested pLO2 and designated pLO2-phaCv or pEB11 and transferred into *E. coli* YMC9 (F-.DELTA.lacU169 thi endA hsdR) by transformation using electroporation. The *E. coli* strain was purified and mixed with *Sphingomonas elodea* strain S-60wtc, along with an *E. coli* strain JZ279 carrying plasmid pRK2013, which supplies functions for conjugal transfer (Ditta, et al., Proc. Natl. Acad. Sci. USA, 77:7347-7351 (1980)). S-60wtc is a derivative of the strain *S. elodea*, ATCC 31461, which was selected as a spontaneous isolate with increased ability to take up plasmid DNA. The conjugal transfer was conducted using stationary phase (overnight) cultures, i.e. 1 ml YMC9/pLO2-phaC.DELTA., 1 ml JZ279/pRK2013 and 2-3 ml *Sphingomonas elodea*. Cultures were mixed and concentrated on a filter, which was in turn placed on a TYE Petri dish (8 g/l tryptone, 5 g/l yeast extract, and 5 g/l sodium chloride) and incubated 37° C. for 7 hours. Cells were then suspended in deionized water and plated on selective media.

After about 7 hrs incubation, kanamycin resistant transconjugants of S-60wtc were selected on YM media (yeast extract 3 g/L, malt extract 3 g/L, peptone 5 g/L and glucose 10 g/L) with 25 .mu.g/ml streptomycin (to counter-select *E. coli*) and 7.5 .mu.g/ml kanamycin to select for the plasmid. Integration, as measured by kanamycin resistance, occurred at a frequency of $1.5 \times 10^{-6}$.

Example 5

Selection for Second Crossover Deletion Strains

Figure 7:
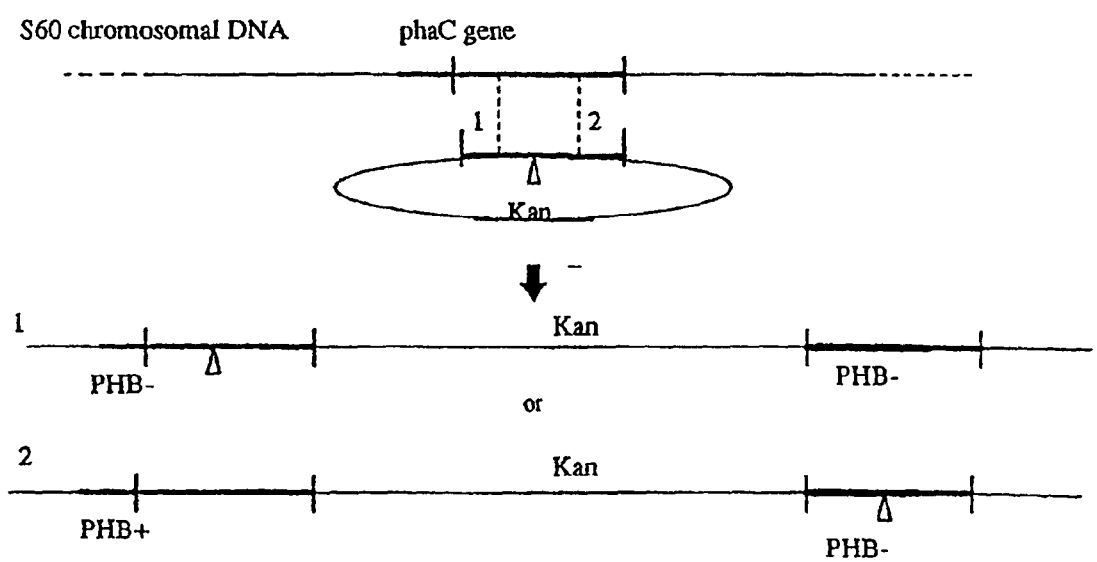
FIG. 7 is a schematic diagram demonstrating integration of a vector containing a phaC deletion into a *Sphingomonas elodea* chromosome.

Two kanamycin-resistant integrants were purified and passed three times in non-selective YEME medium (0.25% yeast extract, 0.025% malt extract), then plated on 7.5% sucrose to select for crossouts. Seven kanamycin-sensitive crossouts were obtained, but all were PHB-positive. A PCR test was used to verify that the vector phaCv was inserted into the phaC region of the chromosome and to determine the location of the insert relative to the wild-type phaC genes. Primers homologous to regions flanking the deletion and to the ends of the vector were designed. Recombination may occur in two orientations that result in: (1) the phaC gene with a deletion to the left and a fragment of the phaC gene to the right of the vector, which should yield a PHB-negative clone; or (2) intact phaC gene to the left and phaCv to the right of the vector, which should yield a PHB-positive clone as depicted in FIG. 7.

Tests on six of the pLO2phaCv single crossover integrants demonstrated that all were in the second, possibly favored, PHB-positive, orientation. There may be a strong preference for recombination on one side of the deletion, or, alternatively, the PHB-positive strain may grow better than the PHB-negative recombinant. Colonies in which the plasmid had integrated in the less preferred manner of the first, PHB-negative, orientation might be more likely to undergo a second recombination event at the preferred site resulting in a double crossover retaining the mutant phenotype.

The transconjugants were screened by PCR and tested for PHB expression to identify integrants in the first, or PHB-negative, orientation. Of 24 colonies tested, PCR results demonstrated that 21 were PHB-positive and three were PHB-negative integrants. PHB tests confirmed the results. The three PHB-negative strains (3, 15 and 22) were selected, purified, grown for three passages under non-selective conditions and plated on sucrose. Of five kanamycin-sensitive colonies from each parent, one was PHB-negative. Thus, three PHB deficient, kanamycin-sensitive mutants were isolated and designated NPG-1, NPG-2 and NPG-3.

Example 6

Characterization of Mutants for Gellan Biosynthesis

NPG-1, NPG-2 and NPG-3 were tested in 10 L fermentations conducted in 14 L fermentors and compared to LPG-2, which is a PHB-deficient mutant isolated by chemical mutagenesis (U.S. Pat. No. 5,300,429). The stages of fermentation and media used were similar to those described in U.S. Pat. No. 5,300,429, except that stage 2 medium was used for all seed stages. Three seed stages were used prior to inoculation of the final medium. Transfer volumes were 2.5-5%. A different organic nitrogen was used (Quest Nzamine EKC, Chicago, Ill., at 0.41 g/L) instead of promosoy at 0.5 g/L. Corn syrup level was 3% instead of 3.75% in the seed stages. The final 10 L fermentation was similar to the seed media, but contained less phosphate (0.5 g/L $K_2HPO_4$) and the pH was controlled by addition of KOH as required. Organic nitrogen was higher (1.1 g/L) as was inorganic nitrogen, $NaNO_3$ (1.5 g/L). Anti-foam H-60-K was added to 0.6 ml/L. The corn syrup level was 3.85%. The medium in the final stage was made up in deionized water supplemented with calcium and magnesium.

The NPG mutants produced significantly less gellan than LPG-2, based on total precipitable material ("TPM") and viscosity, as shown in Table 1. Broth viscosity was determined in a Brookfield viscometer with number 4 spindle at 60 rpm. Total precipitable material was determined by heating broth in an autoclave for ten minutes, then precipitating with two times volume of isopropanol and drying. These results were reproducible. Analysis of broth samples during the fermentation indicated that a large amount of organic acids were produced. Consequently, the low yield of gellan for the NPG mutants correlates with a greater amount of carbohydrate hydrolysis to two and three carbon intermediates and carbon dioxide in the absence of PHB synthesis.

TABLE 1

Summary of 10 L Fermentation Darta for NPG Strains

| Strain | % LPG-2 (TPM) | Visc. cP |
|---|---|---|
| LPG-2 |  | 7,000 |
| NPG-1 | 40 | 1,450 |
| NPG-2 | 45 | 2,200 |
| NPG-3 | 61 | 2,150 |

Example 7

Isolation of Mutants with Restored Gellan Productivity

Figure 8:
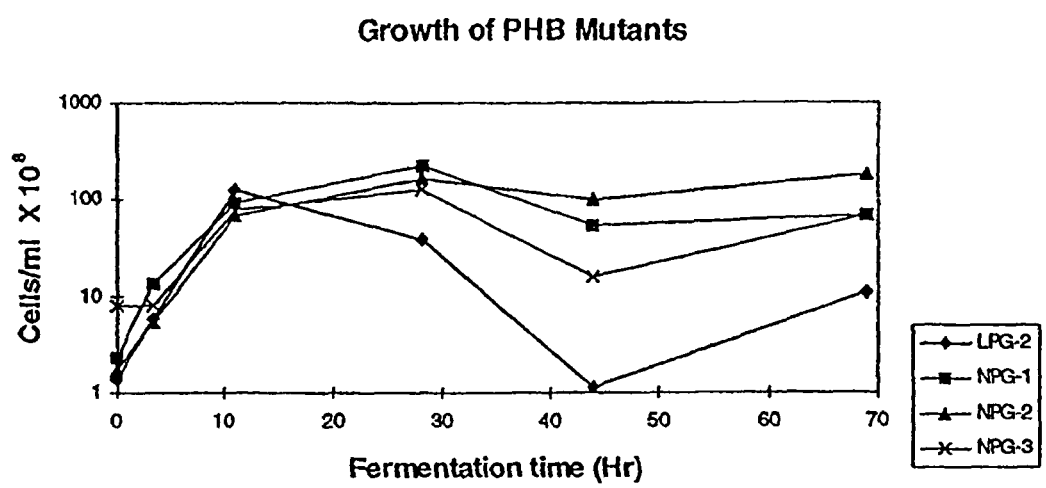
FIG. 8 is a graphical representation of cell counts determined by plating broth samples from 10 L fermentations.

The accumulation of metabolic intermediates (e.g., organic acids) due to the blockage of PHB synthesis may have an adverse effect on gellan synthesis. It was expected that during growth in a medium that promotes gellan synthesis, a compensatory mutation could occur that allows gellan synthesis to proceed at normal levels. Aliquots of fermentation broth from the 10 L fermentations (Example 6), were plated to determine cell counts (FIG. 8). It was observed that towards the end of the fermentation (i.e., at 44 and 69 hours) between about 0.5% and 2% of the colonies were larger and more mucoid than the NPG strains. These colonies were purified and tested for PHB and gellan production in shake flask fermentations. The new isolates were PHB-deficient and had a higher yield of gellan than the original NPG mutants. The best compensatory mutants had total precipitable material comparable to LPG-2 and .gtoreq.80% of the wild type (an approximate 10-15% decrease in TPM is expected due to the loss of weight of PHB.). These strains were designated PDG mutants: PDG-1 is derived from NPG-1, and PDG-3 is derived from NPG-3. Each of the strains was evaluated in shake flask fermentations for PHB and gellan production.

TABLE 2

Shake Flask Fermentation for PHB-Deficient Strains

| Strain | TPM g/100 ml | % S60 | % LPG2 | PHB |
|---|---|---|---|---|
| S60-wtc | 1.52 | | | + |
| LPG-2 | 1.42 | 93 | | − |
| NPG-1 | 0.72 | 47 | 50 | − |
| PDG-1 | 1.44 | 94 | 102 | − |
| NPG-3 | 0.51 | 34 | 36 | − |
| PDG-3 | 1.37 | 90 | 96 | − |

In addition, broth viscosities of a second batch of S60-wtc, LPG-2, PDG-1 and PDG-3 were determined using a Brookfield viscometer with number 4 spindle at 60 rpm. The broth viscosities are shown in Table 3 below.

TABLE 3

Experiment 2
Broth Viscosities f PHB-Deficient Strains

| Strain | Visc. $cP^a \times 10^3$ |
|---|---|
| S60-wtc | 84 |
| LPG-2 | 92 |
| PDG-1 | 83 |
| PDG-3 | 63 |

The media used for shake flasks was similar to that described in U.S. Pat. No. 5,300,429. The first seed contained YM medium. Second and final stages were 100 ml per 500 ml shake flasks, containing medium as described previously, but with higher phosphate for buffering ($K_2HPO_4$, 2.8 g/L; $KH_2PO_4$, 1.2 g/L) and organic nitrogen at 1.0 g/L.

Without being bound by theory, the new mutations may be spontaneous mutants which limit the breakdown of glucose to organic acids. Analysis of in-cycle samples from fermentors indicated that production of organic acids with PDG-1 and PDG-3 was about the same as that of the control strains, S-60wtc and LPG-2.

Strain PDG-1 consistently produced good yield of high viscosity gellan with a TPM>14 g/L.

Colony morphology on plates of these cultures was evaluated to check stability of the strains and particularly, to compare the spontaneous PDG-1 mutants to the original NPG strains which had low gellan yields. After growth on YM agar at about 37° C. for about 60 hours, PDG-1 showed distinctly different morphology than its parent NPG-1. Colonies with NPG-1 type morphology were not observed in broth from PDG-1 fermentations, which indicates the stability of the strain.

Example 8

Presence of Homologous phaC Genes in Sphingomonas Strains Other than S. elodea

Genes homologous to phaC were identified in strains of Sphingomonas other than Sphingomonas elodea thereby demonstrating the feasibility of generating PHB-deficient mutants in strains of Sphingomonas other than Sphingomonas elodea.

Southern DNA hybridization was conducted with four Sphingomonas strains: ATCC 53159, which produces diutan (S-657); ATCC 31555, which produces welan (S-130); ATCC 31961, which produces rhamsan (S-194); and ATCC 31461, which produces gellan (S-60) as control. Genomic DNA was isolated from each strain and digested with the enzyme EcoRI. Samples of digested genomic DNA (1 .mu.g) were separated on a 1% agarose gel and transferred to nylon membranes via capillary action using a Schleicher and Schuell Turboblotter® (Keene, N.H.) under neutral conditions.

Using degenerate primers PHADG5 and PHADG7 (see example 1), a digoxigenin-labeled probe was prepared by PCR-amplification of an internal region of the Sphingomonas S-657 phaC gene with digoxigenin-11-dUTP according to the protocol of the manufacturer, Roche Molecular Biochemicals, Switzerland. Hybridization was conducted under neutral conditions using DigEasyHyb® from Roche Diagnostics (Mannheim, Germany) according to the protocol of the manufacturer. The filters were hybridized at 44° C., which is 10° C. lower than the calculated T.sub.opt. These conditions are expected to result in hybridization of DNA molecules that are more than 90% identical (Birren, B., et al., Eds. Genomic Analysis, A Laboratory Manual, (1997). As used herein, the term T.sub.opt is defined as T.sub.m-20, where T.sub.m is defined by the formula 50+0.41(% GC)−600/probe length, where the % GC is 65% and the probe length is 400 nucleotides. The filters were washed in 2.times. SSC, 0.1% SDS two times for 15 minutes at 44° C. and developed using an anti-digoxigenin-alkaline phosphatase conjugate and a digoxigenin detection kit according to the manufacturer's protocol (Roche Molecular Biochemicals).

Figure 9:
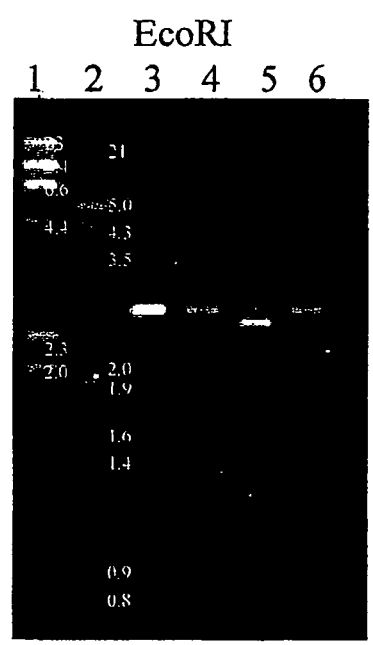
FIG. 9 shows a Southern hybridization of *Sphingomonas* genomic DNA preparations digested with EcoRI and hybridized to a probe for the ATCC 53159 phaC gene. Lanes 1 and 2 contain size markers (.lamda. HindIII and .lamda. HindIII+EcoRI, respectively). Lanes 3-6 contain genomic DNA digests from *Sphingomonas* sp. strains ATCC 53159, 31461, 31555 and 31961, respectively.

The results of the hybridization are shown in FIG. 9. An EcoRI-digested band of the expected size (2.6 kB) was detected in the Sphingomonas strains ATCC 31461. Sphingomonas strains ATCC 53159 and ATCC 31961 produced a band of exactly the same size. Sphingomonas ATCC 31555 contained a 2.4 kB fragment that hybridized to the phaC probe. Thus, the Southern DNA hybridization confirmed that these three strains contain a phaC-like gene and that PHB-deficient strains could be generated according to the methods described herein.

Example 9

Construction of Mutant Strains of ATCC 53159 Having phaC Deletions

Using recombinant DNA techniques, mutant strains of Sphingomonas ATCC 53159 were constructed in which the phaC gene was completely deleted. The construction of the mutant strain was performed as follows: DNA regions flanking the phaC gene were amplified by PCR and cloned into a suicide vector, the suicide vector containing the flanking PCR products was transferred by conjugation into ATCC 53159 cells, then integration of the entire plasmid at a homologous locus directly upstream or downstream of phaC in the Sphingomonas ATCC 53159 chromosome was achieved by selection for kanamycin resistance (as encoded by the vector). Excision of the phaC locus plus the vector DNA from the chromosome was a result of a subsequent second cross-over event which was selected for by sucrose-sensitivity encoded on the vector.

To isolate clones containing the phaC gene and flanking regions, genomic DNA libraries were prepared and screened by PCR, using PHADG5 and PHADG7 primers (see Example 1 above). Two genomic libraries were made, one with NotI restriction enzyme fragments in vector pZERO-2 (Invitrogen, Carlsbad, Calif.), the second with Sau3A partial digest fragments in pLAFR3 (Staskawicz et al. J. Bacteriol. 169:5789-94 (1987)). One positive clone was isolated from each library. BamHI-NotI fragments from these plasmids were subcloned and appropriate fragments sequenced to determine the DNA sequence of the phaC gene and the 5' and 3' flanking regions. Plasmids p21-7 and pJCS104-2 contain respectively, the 5' and 3' ends of the phaC gene and flanking regions.

Figure 11:
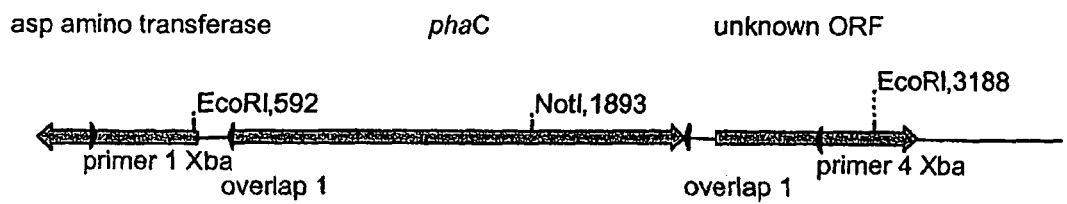
FIG. 11 depicts a genetic map of the phaC region and primers for PCR amplification.

The DNA sequences of the phaC gene and flanking regions are shown in FIG. 10. A genetic map is shown in FIG. 11. Open reading frames were determined by the presence of start and stop codons and BLAST analysis combined with the predicted coding regions using Borodovsky analysis (Lasergene GeneQuest module) and the P_aeruginosa.sub.-3.mat matrix from GeneMark. The sequence is linked from the insert sequences in clones p21-7 and pJCS104-2. The junction between the two sequences is at the NotI site.

Figure 12:
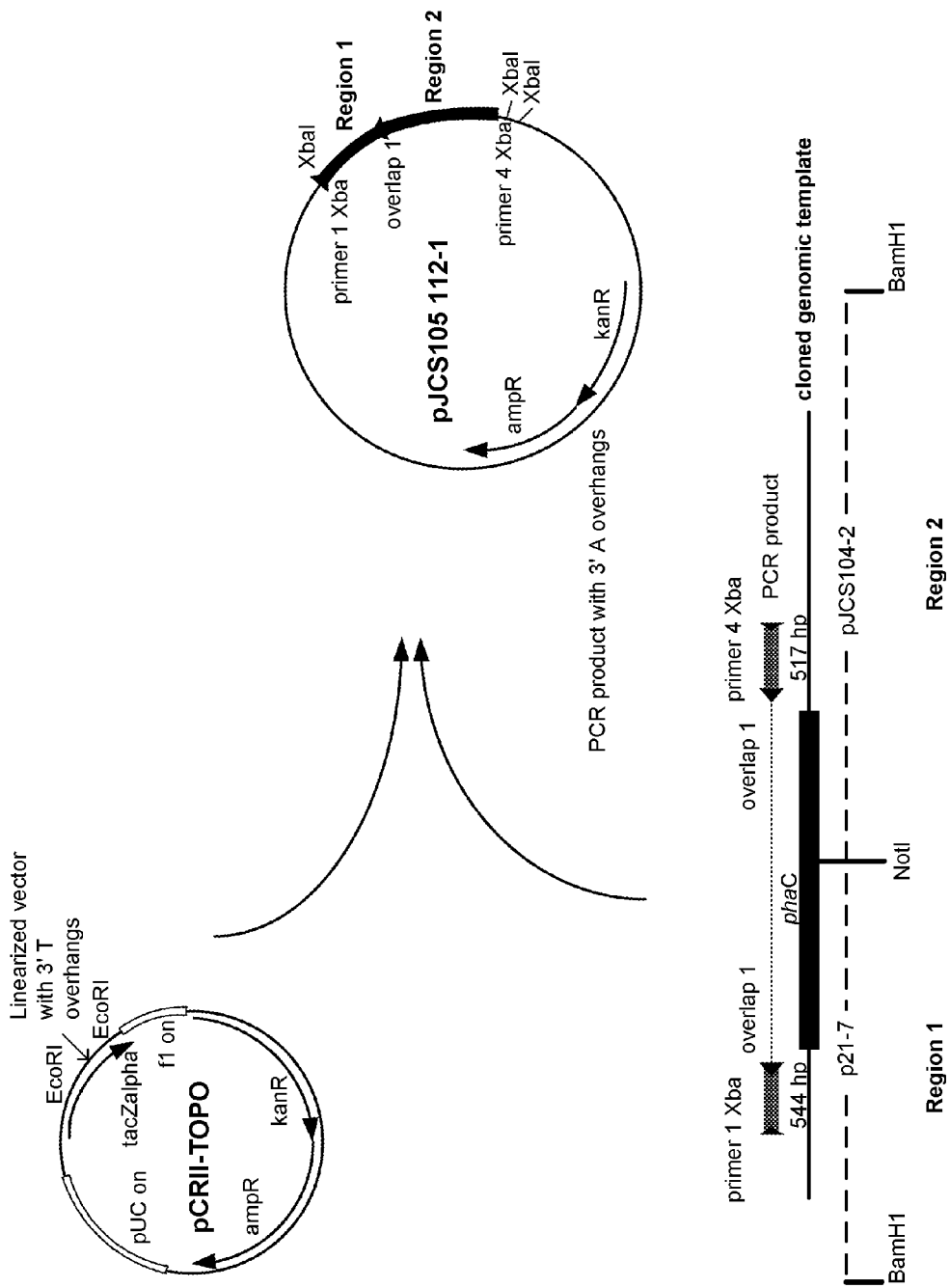
FIG. 12 depicts the cloning strategy in which PCR was used to construct a product containing only the regions flanking phaC and omitting the entire phaC gene.

FIG. 12 depicts how PCR was used to make a product pJCS105 112-1 that contains only the regions flanking phaC, deleting the entire phaC gene (1737 bp) from the first nucleotide of the start codon to the last nucleotide of the stop codon. Two outer primers (primer 1Xba and primer 4Xba) were combined with a primer (overlap1) that spans the desired junction between the upstream and downstream regions of phaC. Primer sequences are shown in Table 4.

Inc. (Palo Alto, Calif.) as per manufacturer's protocol. Amplification was then conducted for 1 min 95° C., 5 cycles of 30 sec at 95° C., 30 sec 44° C., 2 min 68° C., then 20 cycles of 30 sec 95° C., 30 sec 53-68° C., 2 min 68° C., followed by single cycle of 3 min 68° C., in a Matrix thermocycler. The amplified DNA fragment was purified from a gel and further amplified with the same primers to produce more product. The amplification conditions were 1 min 95° C., 25 cycles of 30 sec at 95° C., 30 sec 64° C. 2 min 68° C., then a single cycle at 68° C. A 1.1 kB band was then isolated from the gel using SNAP gel Purification Kit® (Invitrogen) and cloned into vector pCRII-TOPO (Invitrogen) by using topoisomerase, a vector with 3' T overhangs and chemically competent TOP10 cells, according to Invitrogen protocol, to form pJC105-112-1 as shown in FIG. 12.

The 1.1 kB XbaI fragment containing the phaC deletion construct from pJCS105 112-1 was gel purified and cloned into XbaI-digested pLO2. Two orientation of the insert were recovered and designated pJCS106-5 and pJC106-16.

Marker exchange was used to make a PHB-deficient strain of ATCC 53159 Plasmids pJCS106-5 and pJC106-16 were introduced to ATCC 53159 by transconjugation, as per Example 4 above. Selection for the first and second crossover deletion strains proceeded as by examples 4 and 5 above, i.e., selecting first for integration as shown by kanamycin resistance and then plating on sucrose to select for kanamycin sensitive crosscuts. The deletion crossouts (versus wild-type) were detected by diagnostic PCR, and designated NPD-3 (derived from pJCS106-5) and NPD-6 (derived from pJCS106-16.

The resulting NPD-3 and NPD-6 strains have a precise chromosomal deletion of phaC with no foreign DNA remaining. The gum yields of these deletion strains were greatly reduced however, but suppressors that restored gum production were subsequently isolated upon growing in fermentation.

NPD-3 and NPD-6 were grown under conditions to promote S-657 synthesis, and suppressor strains having large, mucoid colonies were selected, as was done for gellan synthesis in Example 7 above. These large, mucoid colonies were designated PDD-3 and PDD-6, as per the colonies from which they were derived, and were analyzed for PHB and S-657 production. The PDD-3 and PDD-6 strains are on deposit with the American Type Culture Collection and designated as ATCC No. PTA-4865 and ATCC No. PTA-

TABLE 4

Primer Sequences for ATCC 53159 phaC deletion

| Primer | Nucleotides (5'_3') (Restriction enzyme site underlined) | Primer-binding Sites | Restriction Site Added |
|---|---|---|---|
| primer 1Xba | ATTCTAGAGATGATGAAGC CGAAGGTGTGGAT (SEQ ID NO: 14) | 537 by upstream of phaC | XbaI |
| primer 4Xba1 | ATTCTAGATGGTGCGCTCG TTGAGG (SEQ ID NO: 15) | 512 by downstream of phaC | XbaI |
| overlap 1 | GAAATTCTGCCTCTTTGTC GGTCCTCTCCTTCGC (SEQ ID NO: 16) | spans the phaC gene open reading frame | none |

Plasmids pJCS104-2 and p21-7 (200 ng each) were mixed with primers 1Xba and 4Xba (50 pmol each), the overlap1 primer (2 pmol), dNTPs and Taq polymerase from Advantage High Fidelity 2 PCR kit from Clontech Laboratories, 4866, respectively both deposited on Dec. 20, 2002. Table 5 below, indicates that PDD-6 provided greater gum production than its predecessor NPD-6 strain while also qualitatively producing no PHB.

TABLE 5

Fermentation Results for
S-657 PHB-Deficient Strains

| Strain | TPM g/L | | |
|---|---|---|---|
| S657 | 20.7 | | + |
| NPD-6 | 5.6 | 27% | − |
| PDD-6 | 18.7 | 90% | − |

Example 10

Effect of Potassium Hydroxide Concentration on Transmittance and Gel Strength

Figure 13:
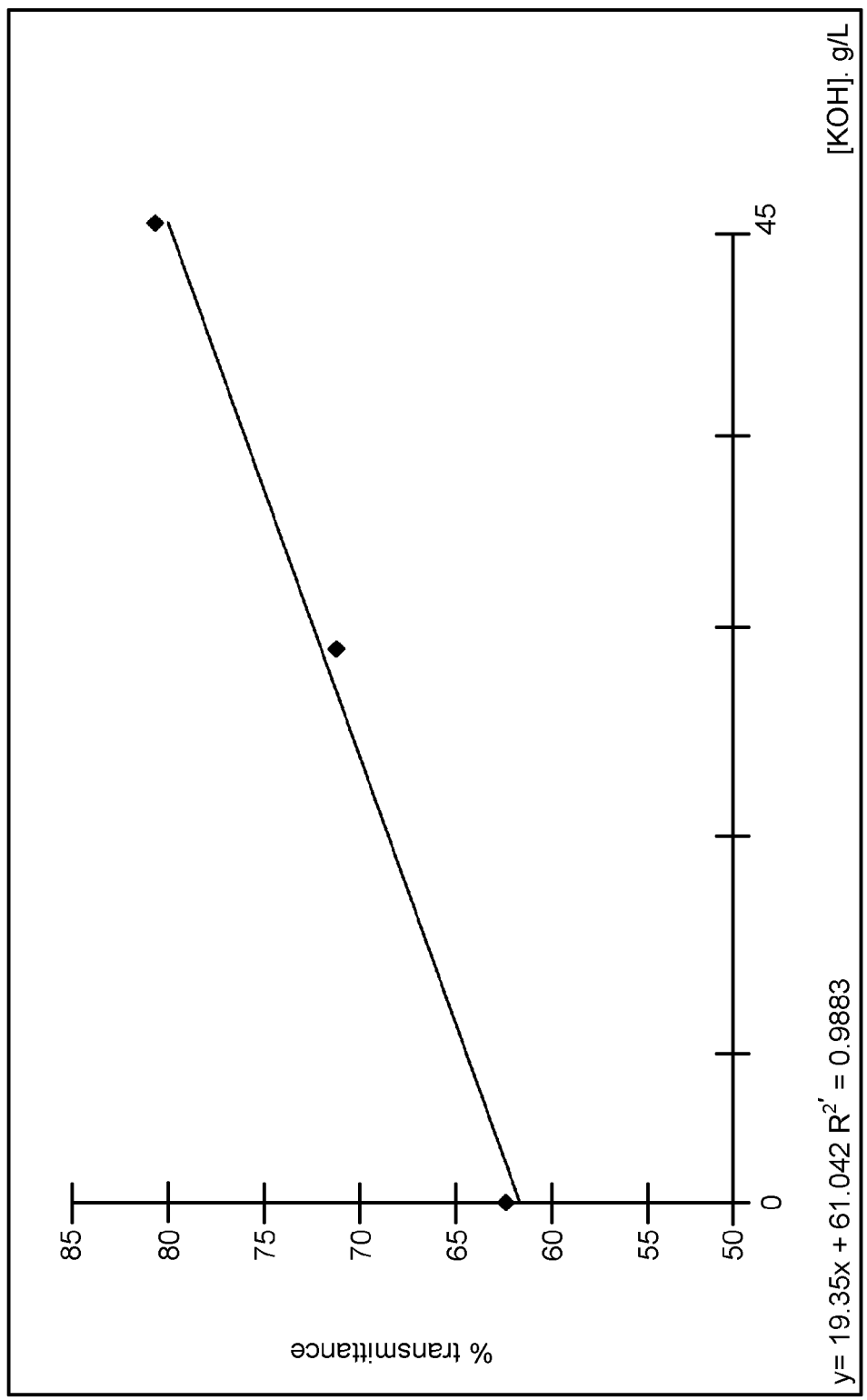
FIG. 13 is a graphical representation of the effect of potassium hydroxide concentration on transmittance.

The effect of the concentration of the caustic agent potassium hydroxide ("KOH") was assessed in the clarification process comprising the steps outlined above as the first protocol. A gellan fermentation broth comprising a PHB-deficient mutant was pretreated and mixed with varying concentrations of KOH for 15 min, followed by 1000 ppm Calgon as chelating agent for 1 hr, followed sequentially by 22 ppm lysozyme and 220 ppm protease for 2 hrs each at 55° C. The KOH concentration tested varied between about 0.0 g/L and about 0.45 g/L. As depicted in FIG. 13, transmittance increased nearly 20% (31% relative increase) as the concentration of KOH increased to 0.45 g/L.

Figure 14:
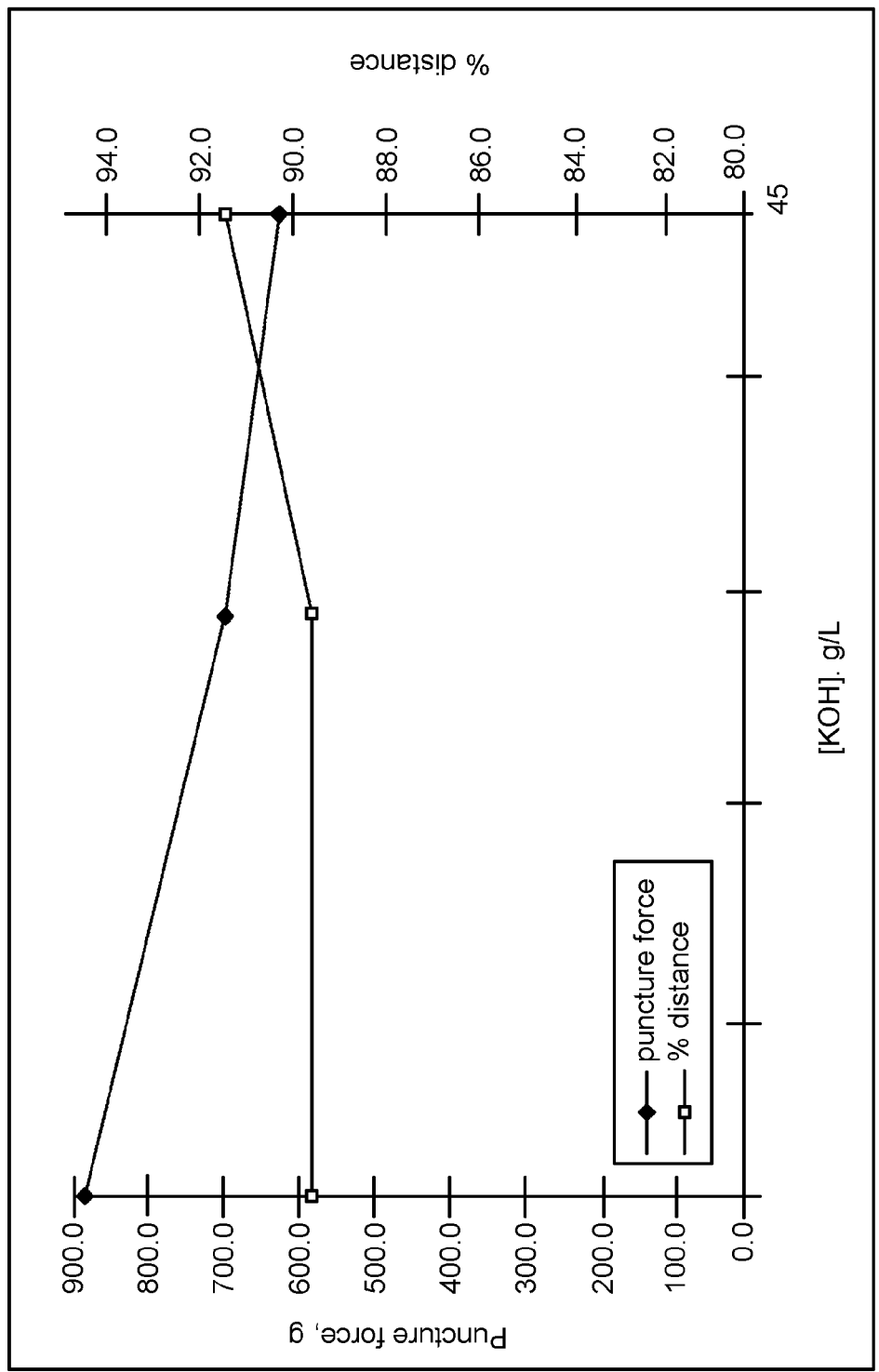
FIG. 14 is a graphical representation of the effect of potassium hydroxide concentration on gel strength.

The TA-TX2 Texture Analyzer® (Texture Technologies Corp., Scarsdale, N.Y.) measures gel strength data as a product of two indicators, the amount of puncture force and distance required to fracture a prepared gel surface with a pressure-sensing plunger. Puncture force is determined when a load cell detects a break in the gel surface, and puncture force is determined as a percent change in height. As depicted in FIG. 14, gel strength with respect to puncture force decreased 280 g, or 32%, over the same range of KOH tested, which may be attributed to the partial deacylation of the gellan. However, gel strength with respect to percent distance did not seem to be significantly affected, reflecting only a 1.5% change.

A small 2x2 factorial study was conducted according to the first protocol clarification process. A gellan fermentation broth comprising a PHB-deficient mutant was pretreated and mixed with varying concentrations of KOH for 15 min, followed by 2000 ppm Calgon as chelating agent for 1 hr, followed sequentially by 22 ppm lysozyme and 220 ppm protease for 2 hrs each at 55° C. In this study, percent transmittance, puncture force and percent distance were studied because they are believed to be interrelated to kinetics. The KOH concentration varied between about 0.225 g/L and about 0.45 g/L, and the temperature varied between about 55° C. and about 60° C. to produce the results shown in the following tables, which demonstrate the percent transmittance, puncture force and percent distance results evaluating the effect of KOH concentration and temperature on gellan clarification.

TABLE 3

| Temp. | [KOH] 0.225 g/L | [KOH] 0.45 g/L |
|---|---|---|
| | Percent transmission | |
| 55° C. | 78.05 | 77.9 |
| 60° C. | 80.9 | 84.2 |
| | Puncture Force | |
| 55° C. | 753 | 562 |
| 60° C. | 600 | 428 |
| | Distance | |
| 55° C. | 89.2 | 87.2 |
| 60° C. | 90.7 | 88.2 |

As demonstrated in the tables, the transmittance did not change much upon increasing either the KOH concentration or temperature separately. However, transmittance increased by about 6% when both KOH concentration and temperature were increased, which indicates that both parameters are critical and additive for achieving increased transmittance. Similarly, gel strength exhibited an additive effect. Puncture force decreased by about 130 g to about 190 g upon increasing either the temperature or KOH concentration individually; however, upon increasing both temperature and KOH concentration, the puncture force was reduced by about 326 g, thus suggesting that gel strength is susceptible to changes in both temperature and KOH concentration.

Example 11

Effect of Sodium Hexametaphosphate on Gellan Properties

Figure 15:
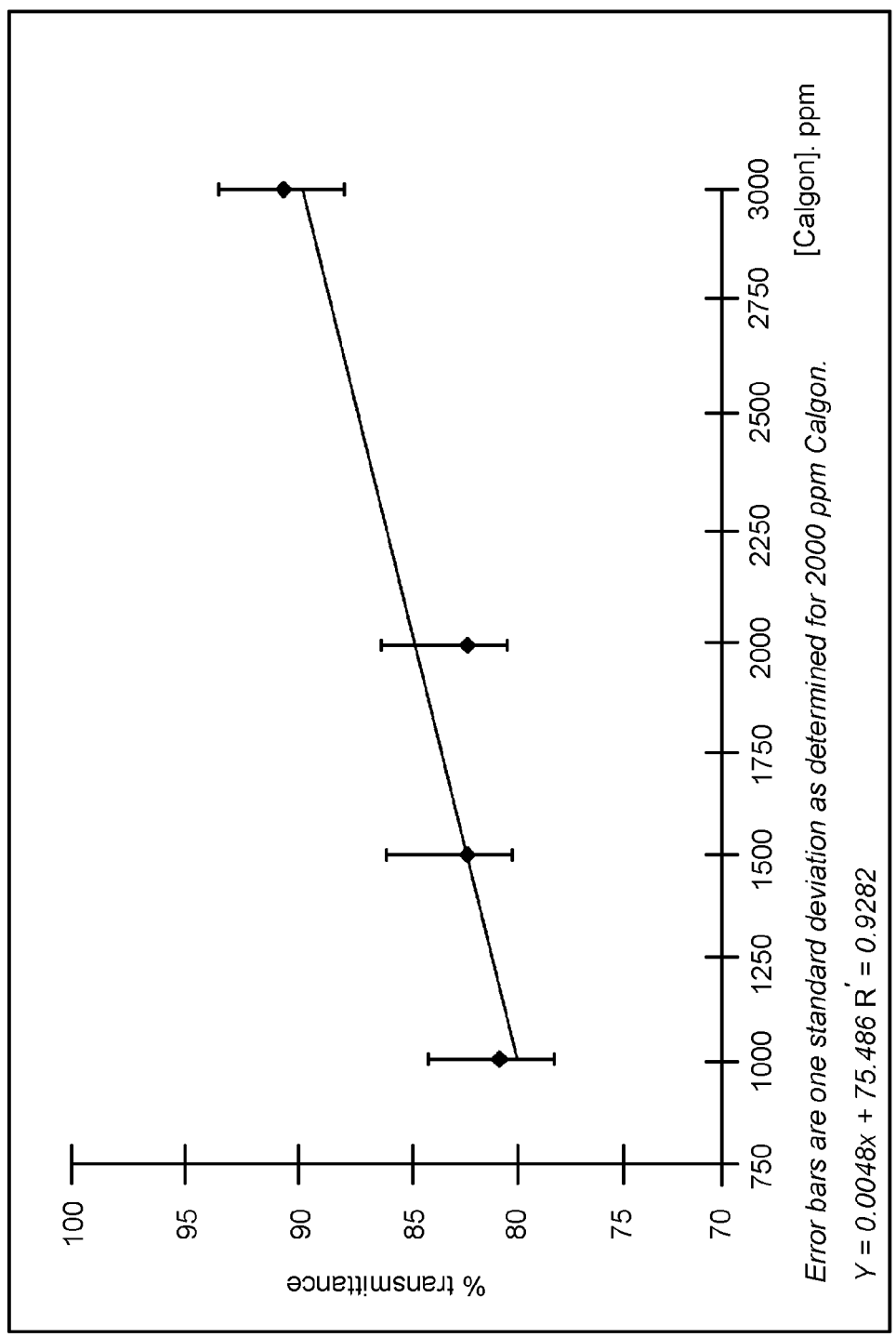
FIG. 15 is a graphical representation of the effect of Calgon concentration on transmittance.
Figure 16:
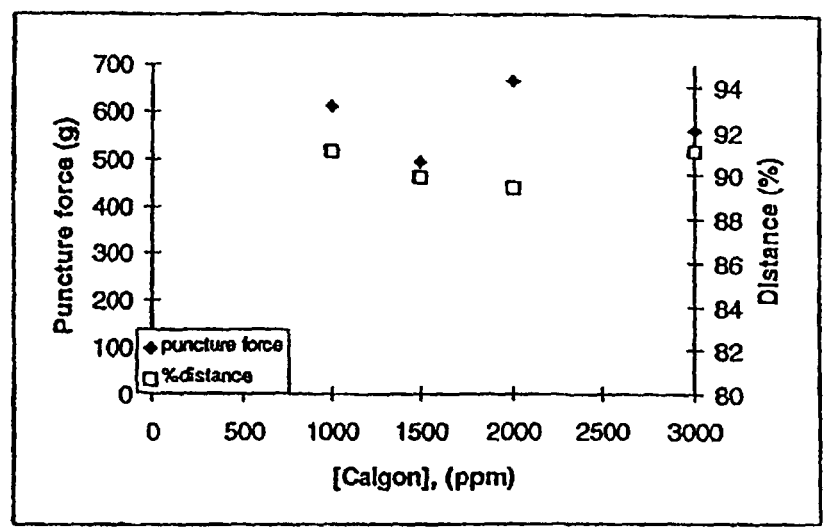
FIG. 16 is a graphical representation of the effect of Calgon concentration on gel strength.

The effect of sodium hexametaphosphate ("SHMP"), which is also known as Calgon, on transmittance, puncture force and percent distance was evaluated according to the clarification process described in Example 10 above. A gellan fermentation broth comprising a PHB-deficient mutant was pretreated and mixed with 0.45 g/L KOH for 15 min, followed by varying concentrations of Calgon for 1 hr, followed sequentially by 22 ppm lysozyme and 220 ppm protease for 2 hrs each at 55° C. SHMP concentration varied between about 1000 ppm and about 3000 ppm, and as demonstrated in FIG. 15, a linear correlation exists between SHMP concentration and transmittance over this range. An increase of about 1000 ppm SHMP results in an about 5% increase in transmittance. As shown in FIG. 16, SHMP does not appear to affect gel strength because both puncture force and percent distance are relatively unaffected by the increase in SHMP concentration over the range tested.

Example 12

Alternative Clarification Sequences with SHMP

Two variations of the clarification method were conducted on native gellan broth at the 2 L scale. According to information supplied by the manufacturer Genencor International, Inc. (Rochester, N.Y.), Multifect® lysozyme is stable at acidic to neutral pH levels and can be inactivated at alkaline pH within a short period of time. After addition of 0.45 g/L KOH according to the clarification process, the pH generally exceeds pH 8, which is sub-optimal for lysozyme, while protease purportedly works well under these conditions. Thus, the clarification process was modified as per the second protocol, to add KOH after the treatment with lysozyme enzyme (sequence summary: lysozyme, then KOH, then protease). Whether KOH was added before or after lysozyme enzyme treatment, a 5.5% relative standard deviation ("RSD") was observed, as shown in the following table.

TABLE 5

|  | Protocol; [SHMP] | Trans (%) | Force (g) | Dist. (%) | N = |
|---|---|---|---|---|---|
| Mean | First protocol; | 82.38 | 436.85 | 87.84 | 4 |
| RSD | 2000 ppm SHMP | 5.50 | 0.28 | 0.02 |  |
| Mean | Second protocol; | 81.34 | **** | **** | 6 |
| RSD | 2000 ppm SHMP | 5.40 |  |  |  |
| Mean | Second protocol; | 83.83 | **** | **** | 3 |
| RSD | 1500 ppm SHMP | 7.10 |  |  |  |

**** refers to unmeasured data RSD refers to relative standard deviation as a percentage of the mean.

Example 13

Confection Formulation

This example demonstrates a formulation that may be used to produce an elastic and resilient chewy confection that exhibits excellent clarity and stability.

| Ingredients | Percent |
|---|---|
| Part A | |
| Glucose syrup | 45.00 |
| Water | 21.67 |
| Part B | |
| Sucrose | 30.00 |
| Clarified high-acyl gellan | 1.33 |
| Kelcogel F ® gellan | 0.67 |
| (CP Kelco U.S., Inc., San Diego, CA) | |
| Part C | |
| Citric acid solution, 54% | 0.67 |
| Sodium citrate solution, 33% | 0.67 |

The components comprising Part A were combined in a heating vessel and heated to 40° C.

The components of Part B were blended dry and added to the heating vessel mixed rapidly, and brought to boil. The mixture was reduced to 72% solids. The components of Part C were combined and added to flavor and color, and mixed until homogeneous.

The material was placed into a depositer and casted into prepared starch molds. The filled starch molds were then stored at 30° C. and 35% relative humidity for 3 to 4 days until the solids level reached between about 82% and 85%. The material was de-molded, waxed and stored in sealed bags.

Additional water may be added to the Part A ingredients to facilitate complete hydration of the hydrocolloids.

Example 14

Dessert Gel Formulation

This formulation was used to produce an elastic and resilient dessert gel with excellent clarity and stability.

| Ingredients | Percent |
|---|---|
| Part A | |
| Sucrose | 13.20 |
| Adipic acid | 0.40 |
| Clarified, high-acyl gellan | 0.16 |
| Sodium citrate | 0.13 |
| Disodium phosphate | 0.13 |
| Fumaric Acid | 0.11 |
| Kelcogel F ® gellan | 0.04 |
| (CP Kelco U.S., Inc., San Diego, CA) | |
| Part B | |
| Water | 85.83 |

The ingredients of Part A, in addition to dry flavor and color, were blended dry and dispersed into Part B and mixed; heated to 90° C. The mixture was then poured into suitable containers and allowed to set at room temperature.

Example 15

Jelly Formulation

This formulation provided a jelly with excellent clarity, storage stability, flavor release and spread-ability.

| Ingredients | Percent |
|---|---|
| Part A | |
| Concord grape juice | 45.69 |
| High fructose corn syrup | 30.46 |
| Water | 22.85 |
| Part B | |
| Clarified, high-acyl gellan | 0.18 |
| Sodium citrate | 0.10 |
| SHMP | 0.10 |
| Potassium sorbate | 0.09 |
| Part C | |
| Citric Acid, 50% solution | 0.58 |

The ingredients of Part A were combined. The ingredients of Part B were blended dry and dispersed with the ingredients of Part A while mixing. The resulting mixture was brought to boil while mixing and held at a boil for about 1 to about 3 minutes, at which point, the ingredients of Part C were stirred into the mixture. The mixture was then deposited into sterilized jars and sealed.

While the present invention is described above with respect to what is currently considered to be its preferred embodiments, it is to be understood that the invention is not limited to that described above. To the contrary, the invention is intended to cover various modifications and equivalent arrangements included within the spirit and scope of the appended claims.

The invention claimed is:

1. A clarified Sphingan product from a *Sphingomonas* mutant strain, wherein a phaC gene in said *Sphingomonas* mutant strain has been selectively mutated such that the mutant strain produces Sphingan without producing polyhydroxybutyrate (PHB) due to lack of expression of phaC protein in said mutant strain, wherein said clarified Sphingan product is PHB-deficient, and said clarified Sphingan product having been clarified by a process using a chelating agent before using a lysozyme, protease, or both.

2. The clarified Sphingan product of claim 1 being clarified by the steps of:
   a) heating an aqueous Sphingan solution containing native Sphingan to a clarification temperature of 30-70° C.,
   b) treating the heated aqueous Sphingan solution from step a) with at least one chelating agent,
   c) treating the Sphingan solution from step b) with a lysozyme enzyme, a protease, or both, and
   d) recovering the clarified Sphingan product by precipitation with an alcohol.

3. The clarified Sphingan product of claim 2, wherein the at least one chelating agent is selected from the group consisting of ethylenediamine tetraacetic acid, phosphoric acid, metaphosphoric acid, carbonic acid, citric acid, tartaric acid, gluconic acid, glutamic acid, pyrophosphoric acid, polyphosphoric acid, metaphosphoric acids, saccharic acid, ethyleneglycol-bis-(beta-aminoethyl ether)-N,N,N',N'-tetraacetic acid (EGTA), ethylenediamine, 2,3-diaminobutane, 1,2-diaminocyclohexane, triaminotriethylamine, and a salt thereof.

4. The clarified Sphingan product of claim 2, wherein the at least one chelating agent is selected from the group consisting of disodium ethylenediamine tetraacetate, dipotassium ethylenediamine tetraacetate, tetrasodium ethylenediamine tetraacetate, tetrapotassium ethylenediamine tetraacetate, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, ethylenediamine dihydroiodide, and mixtures thereof.

5. The clarified Sphingan product of claim 2, wherein the clarification process further comprises a step of treating the Sphingan solution from step c) with at least one caustic agent, an oxidizing agent, or both.

6. The clarified Sphingan product of claim 5, wherein the caustic agent is selected from the group consisting of potassium hydroxide, sodium hydroxide and trisodium phosphate.

7. The clarified Sphingan product of claim 5, wherein the oxidizing agent is selected from the group consisting of sodium hypochlorite or other hypochlorite salts, chloride dioxide, hydrogen peroxide, peracetic acid and ozone.

8. The clarified Sphingan product of claim 2, wherein the clarification process further comprises a step of treating the Sphingan solution from step a) with a surfactant during or after the chelating agent treatment in step b).

9. The clarified Sphingan product of claim 8, wherein the surfactant is selected from the group consisting of SDS, polyoxyethylenesorbitan monooleate, lecithin, a monoglyceride, a tartaric ester of a monoglyceride, a phosphated monoglyceride, a lactylated monoglyceride, an acetylated monoglyceride, a succinylated monoglyceride, an ethoxylated monoglyceride, a sorbitan ester, a polysorbate, a polyglycerol ester, a sucrose ester, a sodium stearoyl lactylate, and a propylene glycol ester.

10. The clarified Sphingan product of claim 2, wherein the treatment with the lysozyme enzyme is conducted at a pH of 3 to 7.5.

11. The clarified Sphingan product of claim 2, wherein the treatment with the protease enzyme is conducted at a pH of 6.5 to 9.

12. The clarified Sphingan product of claim 1, wherein dissolution of the clarified Sphingan product in water at a Sphingan concentration of 1% w/w provides a light transmittance greater than about 60% measured at a wavelength of 600 to 650 nm.

13. The clarified Sphingan product of claim 1, wherein the dissolution of the clarified Sphingan product in water at a Sphingan concentration of 1% w/w provides a light transmittance greater than about 70% measured at a wavelength of 600 to 650 nm.

14. The clarified Sphingan product of claim 1, wherein the dissolution of the clarified Sphingan product in water at a Sphingan concentration of 1% w/w provides a light transmittance greater than about 80% measured at a wavelength of 600 to 650 nm.

15. The clarified Sphingan product of claim 1, wherein the Sphingan is selected from the group consisting of gellan, diutan, welan and rhamsan.

16. The clarified Sphingan product of claim 1, wherein the Sphingan is produced from a *Sphingomonas* mutant strain genetically modified from a wild-type *Sphingomonas* strain ATCC 53159.

* * * * *

SEQUENCE LISTING

<160> NUMBER OF SEQ ID NOS: 16

<210> SEQ ID NO 1
<211> LENGTH: 577
<212> TYPE: PRT
<213> ORGANISM: Rhizobium meliloti

<400> SEQUENCE: 1

```
Met Ala Arg Ala Ala Glu Gln Leu Gly Lys Ala Ser Ala Trp Leu
1               5                   10                  15

Ala Pro Arg Glu Ala Gly Glu Lys Thr Asp Ser Phe Ala Glu Pro Val
            20                  25                  30

Ser Asp Met Val Lys Thr Leu Ser Lys Val Ser Glu Tyr Trp Leu Ser
        35                  40                  45

Asp Pro Arg Arg Thr Leu Glu Ala Gln Thr His Leu Leu Gly Ser Phe
    50                  55                  60

Phe Asp Met Trp Ser Arg Thr Leu Gln Arg Met Ala Ala Asp Ala Val
65                  70                  75                  80

Glu Asp Pro Ala Asn Leu Gln His Asn Asp Lys Arg Phe Ala Asp Glu
                85                  90                  95

Asp Trp Val Lys Asn Pro Phe Phe Asp Phe Ile Arg Gln Ala Tyr Phe
            100                 105                 110

Val Thr Ser Asp Trp Ala Glu Arg Met Val Lys Asp Ala Glu Gly Leu
        115                 120                 125

Asp Asp His Thr Arg His Lys Ala Ala Phe Tyr Val Arg Gln Ile Ala
    130                 135                 140

Ser Ala Leu Ser Pro Thr Asn Phe Ile Thr Thr Asn Pro Gln Leu Tyr
145                 150                 155                 160

Arg Glu Thr Val Ala Ser Ser Gly Ala Asn Leu Val Lys Gly Met Gln
                165                 170                 175

Met Leu Ala Glu Asp Ile Ala Ala Gly Arg Gly Glu Leu Arg Leu Arg
            180                 185                 190

Gln Thr Asp Thr Ser Lys Phe Ala Ile Gly Glu Asn Ile Ala Ile Thr
        195                 200                 205

Pro Gly Lys Val Ile Ala Gln Asn Asp Val Cys Gln Val Leu Gln Tyr
    210                 215                 220

Glu Ala Ser Thr Glu Thr Val Leu Lys Arg Pro Leu Leu Ile Cys Pro
225                 230                 235                 240

Pro Trp Ile Asn Lys Phe Tyr Val Leu Asp Leu Asn Pro Glu Lys Ser
                245                 250                 255

Phe Ile Lys Trp Ala Val Asp Gln Gly Gln Thr Val Phe Val Ile Ser
            260                 265                 270

Trp Val Asn Pro Asp Glu Arg His Ala Ser Lys Asp Trp Glu Ala Tyr
        275                 280                 285

Ala Arg Glu Gly Ile Gly Phe Ala Leu Asp Ile Ile Glu Gln Ala Thr
    290                 295                 300

Gly Glu Arg Glu Val Asn Ser Ile Gly Tyr Cys Val Gly Gly Thr Leu
305                 310                 315                 320

Leu Ala Ala Thr Leu Ala Leu His Ala Ala Glu Gly Asp Glu Arg Ile
                325                 330                 335

Arg Ser Ala Thr Leu Phe Thr Thr Gln Val Asp Phe Thr His Ala Gly
            340                 345                 350

Asp Leu Lys Val Phe Val Asp Asp Gln Ile Arg His Leu Glu Ala
        355                 360                 365
```

-continued

Asn Met Ser Ala Thr Gly Tyr Leu Glu Gly Ser Lys Met Ala Ser Ala
370                 375                 380

Phe Asn Met Leu Arg Ala Ser Glu Leu Ile Trp Pro Tyr Phe Val Asn
385                 390                 395                 400

Asn Tyr Leu Lys Gly Gln Asp Pro Leu Pro Phe Asp Leu Leu Tyr Trp
            405                 410                 415

Asn Ser Asp Ser Thr Arg Met Pro Ala Ala Asn His Ser Phe Tyr Leu
            420                 425                 430

Arg Asn Cys Tyr Leu Glu Asn Arg Leu Ser Arg Gly Glu Met Met Leu
            435                 440                 445

Ala Gly Arg Arg Val Ser Leu Gly Asp Val Lys Ile Pro Ile Tyr Asn
450                 455                 460

Leu Ala Thr Lys Glu Asp His Ile Ala Pro Ala Lys Ser Val Phe Leu
465                 470                 475                 480

Gly Ser Ser Ser Phe Gly Gly Lys Val Thr Phe Val Leu Ser Gly Ser
            485                 490                 495

Gly His Ile Ala Gly Val Val Asn Pro Pro Ala Arg Ser Lys Tyr Gln
            500                 505                 510

Tyr Trp Thr Gly Gly Ala Pro Lys Gly Asp Ile Glu Thr Trp Met Gly
            515                 520                 525

Lys Ala Lys Glu Thr Ala Gly Ser Trp Trp Pro His Trp Gln Gly Trp
530                 535                 540

Val Glu Arg Leu Asp Lys Arg Val Pro Ala Arg Lys Ala Gly Gly
545                 550                 555                 560

Pro Leu Asn Ser Ile Glu Glu Ala Pro Gly Ser Tyr Val Arg Val Arg
            565                 570                 575

Ala

<210> SEQ ID NO 2
<211> LENGTH: 589
<212> TYPE: PRT
<213> ORGANISM: Alcaligenes eutrophus

<400> SEQUENCE: 2

Met Ala Thr Gly Lys Gly Ala Ala Ala Ser Thr Gln Glu Gly Lys Ser
1               5                   10                  15

Gln Pro Phe Lys Val Thr Pro Gly Pro Phe Asp Pro Ala Thr Trp Leu
                20                  25                  30

Glu Trp Ser Arg Gln Trp Gln Gly Thr Glu Gly Asn Gly His Ala Ala
            35                  40                  45

Ala Ser Gly Ile Pro Gly Leu Asp Ala Leu Ala Gly Val Lys Ile Ala
        50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

```
Leu Ala Thr Asn Pro Glu Ala Gln Arg Leu Ile Glu Ser Gly Gly
            165                 170                 175

Glu Ser Leu Arg Ala Gly Val Arg Asn Met Met Glu Asp Leu Thr Arg
        180                 185                 190

Gly Lys Ile Ser Gln Thr Asp Glu Ser Ala Phe Glu Val Gly Arg Asn
    195                 200                 205

Val Ala Val Thr Glu Gly Ala Val Val Phe Glu Asn Glu Tyr Phe Gln
210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
    290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
    450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
    530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
```

-continued

```
<210> SEQ ID NO 3
<211> LENGTH: 590
<212> TYPE: PRT
<213> ORGANISM: Acinetobacter sp. strain RA3849

<400> SEQUENCE: 3

Met Asn Pro Asn Ser Phe Gln Phe Lys Glu Asn Ile Leu Gln Phe Phe
1               5                   10                  15

Ser Val His Asp Asp Ile Trp Lys Lys Leu Gln Glu Phe Tyr Tyr Gly
            20                  25                  30

Gln Ser Pro Ile Asn Glu Ala Leu Ala Gln Leu Asn Lys Glu Asp Met
        35                  40                  45

Ser Leu Phe Phe Glu Ala Leu Ser Lys Asn Pro Ala Arg Met Met Glu
    50                  55                  60

Met Gln Trp Ser Trp Trp Gln Gly Gln Ile Gln Ile Tyr Gln Asn Val
65                  70                  75                  80

Leu Met Arg Ser Val Ala Lys Asp Val Ala Pro Phe Ile Gln Pro Glu
                85                  90                  95

Ser Gly Asp Arg Arg Phe Asn Ser Pro Leu Trp Gln Glu His Pro Asn
            100                 105                 110

Phe Asp Leu Leu Ser Gln Ser Tyr Leu Leu Phe Ser Gln Leu Val Gln
        115                 120                 125

Asn Met Val Asp Val Val Glu Gly Val Pro Asp Lys Val Arg Tyr Arg
130                 135                 140

Ile His Phe Phe Thr Arg Gln Met Ile Asn Ala Leu Ser Pro Ser Asn
145                 150                 155                 160

Phe Leu Trp Thr Asn Pro Glu Val Ile Gln Gln Thr Val Ala Glu Gln
                165                 170                 175

Gly Glu Asn Leu Val Arg Gly Met Gln Val Phe His Asp Asp Val Met
            180                 185                 190

Asn Ser Gly Lys Tyr Leu Ser Ile Arg Met Val Asn Ser Asp Ser Phe
        195                 200                 205

Ser Leu Gly Lys Asp Leu Ala Tyr Thr Pro Gly Ala Val Val Phe Glu
    210                 215                 220

Asn Asp Ile Phe Gln Leu Leu Gln Tyr Glu Ala Thr Thr Glu Asn Val
225                 230                 235                 240

Tyr Gln Thr Pro Ile Leu Val Pro Pro Phe Ile Asn Lys Tyr Tyr
                245                 250                 255

Val Leu Asp Leu Arg Glu Gln Asn Ser Leu Val Asn Trp Leu Arg Gln
            260                 265                 270

Gln Gly His Thr Val Phe Leu Met Ser Trp Arg Asn Pro Asn Ala Glu
        275                 280                 285

Gln Lys Glu Leu Thr Phe Ala Asp Leu Ile Thr Gln Gly Ser Val Glu
    290                 295                 300

Ala Leu Arg Val Ile Glu Gly Ile Thr Gly Glu Lys Glu Ala Asn Cys
305                 310                 315                 320

Ile Gly Tyr Cys Ile Gly Gly Thr Leu Leu Ala Ala Thr Gln Ala Tyr
                325                 330                 335

Tyr Val Ala Lys Arg Leu Lys Asn His Val Lys Ser Ala Thr Tyr Met
            340                 345                 350

Ala Thr Ile Ile Asp Phe Glu Asn Pro Gly Ser Leu Gly Val Phe Ile
        355                 360                 365
```

```
Asn Glu Pro Val Val Ser Gly Leu Glu Asn Leu Asn Gln Leu Gly
    370                 375                 380
Tyr Phe Asp Gly Arg Gln Leu Ala Val Thr Phe Ser Leu Leu Arg Glu
385                 390                 395                 400
Asn Thr Leu Tyr Trp Asn Tyr Tyr Ile Asp Asn Tyr Leu Lys Gly Lys
                405                 410                 415
Glu Pro Ser Asp Phe Asp Ile Leu Tyr Trp Asn Ser Asp Gly Thr Asn
            420                 425                 430
Ile Pro Ala Lys Ile His Asn Phe Leu Arg Asn Leu Tyr Leu Asn
                435                 440                 445
Asn Glu Leu Ile Ser Pro Asn Ala Val Lys Val Asn Gly Val Gly Leu
    450                 455                 460
Asn Leu Ser Arg Val Lys Thr Pro Ser Phe Phe Ile Ala Thr Gln Glu
465                 470                 475                 480
Asp His Ile Ala Leu Trp Asp Thr Cys Phe Arg Gly Ala Asp Tyr Leu
                485                 490                 495
Gly Gly Glu Ser Thr Leu Val Leu Gly Glu Ser Gly His Val Ala Gly
            500                 505                 510
Ile Val Asn Pro Pro Ser Arg Asn Lys Tyr Gly Cys Tyr Thr Asn Ala
                515                 520                 525
Ala Lys Phe Glu Asn Thr Lys Gln Trp Leu Asp Gly Ala Glu Tyr His
    530                 535                 540
Pro Glu Ser Trp Trp Leu Arg Trp Gln Ala Trp Val Thr Pro Tyr Thr
545                 550                 555                 560
Gly Glu Gln Val Pro Ala Arg Asn Leu Gly Asn Ala Gln Tyr Pro Ser
                565                 570                 575
Ile Glu Ala Ala Pro Gly Arg Tyr Val Leu Val Asn Leu Phe
            580                 585                 590

<210> SEQ ID NO 4
<211> LENGTH: 601
<212> TYPE: PRT
<213> ORGANISM: Rhodobacter sphaeroides

<400> SEQUENCE: 4

Met Ala Thr Glu Glu Gln Ser Pro Gly Ser Gly Arg Asp Ala Gln Phe
1               5                   10                  15
Glu Arg Leu Asn Ala Asn Leu Thr Arg Ile Asp Glu Leu Ser Lys Arg
            20                  25                  30
Leu Thr Ala Ala Leu Thr Lys Arg Lys Leu Ser Asp Pro Ala Leu His
        35                  40                  45
Gly Pro Ser Gly Asp Val Phe Leu Lys Ala Met Thr Ala Tyr Met Ala
    50                  55                  60
Glu Met Met Gln Asn Pro Ala Lys Ile Leu Glu His Gln Ile Ser Phe
65                  70                  75                  80
Trp Gly Lys Ser Leu Lys His Tyr Val Glu Ala Gln His Gln Leu Val
                85                  90                  95
Lys Gly Glu Leu Lys Pro Pro Asp Val Thr Pro Lys Asp Arg Arg
            100                 105                 110
Phe Ser Asn Pro Leu Trp Gln Thr His Pro Phe Phe Asn Tyr Leu Lys
        115                 120                 125
Gln Gln Tyr Leu Met Asn Ala Glu Ala Val Asn Gln Ala Val Glu Gly
    130                 135                 140
Leu Glu His Ile Glu Pro Ser Asp Lys Lys Arg Val Glu Tyr Phe Ser
145                 150                 155                 160
```

```
Arg Gln Ile Val Asp Leu Phe Ser Pro Thr Asn Phe Phe Gly Thr Asn
                165                 170                 175

Pro Asp Ala Leu Glu Arg Ala Ile Ala Thr Asp Gly Glu Ser Leu Val
            180                 185                 190

Gln Gly Leu Glu Asn Leu Val Arg Asp Ile Glu Ala Asn Asn Gly Asp
        195                 200                 205

Leu Leu Val Thr Leu Ala Asp Pro Glu Ala Phe Gln Val Gly Gln Asn
    210                 215                 220

Leu Ala Thr Thr Glu Gly Ser Val Val Tyr Arg Asn Arg Met Phe Glu
225                 230                 235                 240

Leu Ile Gln Tyr Lys Pro Thr Thr Glu Thr Val His Glu Thr Pro Leu
                245                 250                 255

Leu Ile Phe Pro Pro Trp Ile Asn Lys Phe Tyr Ile Leu Asp Leu Lys
            260                 265                 270

Pro Gln Asn Ser Leu Leu Lys Trp Leu Val Asp Gln Gly Phe Thr Val
        275                 280                 285

Phe Val Val Ser Trp Val Asn Pro Asp Lys Ser Tyr Ala Gly Ile Gly
    290                 295                 300

Met Asp Asp Tyr Ile Arg Glu Gly Tyr Met Arg Ala Met Ala Glu Val
305                 310                 315                 320

Arg Ser Ile Thr Arg Gln Lys Gln Ile Asn Ala Val Gly Tyr Cys Ile
                325                 330                 335

Ala Gly Thr Thr Leu Thr Leu Thr Leu Ala His Leu Gln Lys Ala Gly
            340                 345                 350

Asp Pro Ser Val Arg Ser Ala Thr Phe Phe Thr Thr Leu Thr Asp Phe
        355                 360                 365

Ser Asp Pro Gly Glu Val Gly Val Phe Leu Asn Asp Asp Phe Val Asp
    370                 375                 380

Gly Ile Glu Arg Gln Val Ala Val Asp Gly Ile Leu Asp Lys Thr Phe
385                 390                 395                 400

Met Ser Arg Thr Phe Ser Tyr Leu Arg Ser Asn Asp Leu Ile Tyr Gln
                405                 410                 415

Pro Ala Ile Lys Ser Tyr Met Met Gly Glu Ala Pro Pro Ala Phe Asp
            420                 425                 430

Leu Leu Tyr Trp Asn Gly Asp Gly Thr Asn Leu Pro Ala Gln Met Ala
        435                 440                 445

Val Glu Tyr Leu Arg Gly Leu Cys Gln Gln Asp Arg Leu Ala Gly Gly
    450                 455                 460

Thr Phe Pro Val Leu Gly Ser Pro Val Gly Leu Lys Asp Val Thr Leu
465                 470                 475                 480

Pro Val Cys Ala Ile Ala Cys Glu Thr Asp His Ile Ala Pro Trp Lys
                485                 490                 495

Ser Ser Phe Asn Gly Phe Arg Gln Phe Gly Ser Thr Asp Lys Thr Phe
            500                 505                 510

Ile Leu Ser Gln Ser Gly His Val Ala Gly Ile Val Asn Pro Pro Ser
        515                 520                 525

Arg Asn Lys Tyr Gly His Tyr Thr Asn Glu Gly Pro Ala Gly Thr Pro
    530                 535                 540

Glu Ser Phe Arg Glu Gly Ala Glu Phe His Ala Gly Ser Trp Trp Pro
545                 550                 555                 560

Arg Trp Gly Ala Trp Leu Ala Glu Arg Ser Gly Lys Gln Val Pro Ala
                565                 570                 575
```

Arg Gln Pro Gly Asp Ser Lys His Pro Glu Leu Ala Pro Pro Gly
          580                 585                 590

Ser Tyr Val Ala Ala Val Gly Gly Ala
          595                 600

<210> SEQ ID NO 5
<211> LENGTH: 605
<212> TYPE: PRT
<213> ORGANISM: Methylobacterium extorquens

<400> SEQUENCE: 5

Met Gly Thr Glu Arg Thr Asn Pro Ala Ala Pro Asp Phe Glu Thr Ile
1               5                   10                  15

Ala Arg Asn Ala Asn Gln Leu Ala Glu Val Phe Arg Gln Ser Ala Ala
            20                  25                  30

Ala Ser Leu Lys Pro Phe Glu Pro Ala Gly Gln Gly Ala Leu Leu Pro
        35                  40                  45

Gly Ala Asn Leu Gln Gly Ala Ser Glu Ile Asp Glu Met Thr Arg Thr
    50                  55                  60

Leu Thr Arg Val Ala Glu Thr Trp Leu Lys Asp Pro Glu Lys Ala Leu
65                  70                  75                  80

Gln Ala Gln Thr Lys Leu Gly Gln Ser Phe Ala Ala Leu Trp Ala Ser
                85                  90                  95

Thr Leu Thr Arg Met Gln Gly Ala Val Thr Glu Pro Val Val Gln Pro
            100                 105                 110

Pro Pro Thr Asp Lys Arg Phe Ala His Ala Asp Trp Ser Ala Asn Pro
        115                 120                 125

Val Phe Asp Leu Ile Lys Gln Ser Tyr Leu Leu Gly Arg Trp Ala
    130                 135                 140

Glu Glu Met Val Glu Thr Ala Glu Gly Ile Asp Glu His Thr Arg His
145                 150                 155                 160

Lys Ala Glu Phe Tyr Leu Arg Gln Leu Leu Ser Ala Tyr Ser Pro Ser
                165                 170                 175

Asn Phe Val Met Thr Asn Pro Glu Leu Leu Arg Gln Thr Leu Glu Glu
            180                 185                 190

Gly Gly Ala Asn Leu Met Arg Gly Met Lys Met Leu Gln Glu Asp Leu
        195                 200                 205

Glu Ala Gly Gly Gly Gln Leu Arg Val Arg Gln Thr Asp Leu Ser Ala
    210                 215                 220

Phe Thr Phe Gly Lys Asp Val Ala Val Thr Pro Gly Glu Val Ile Phe
225                 230                 235                 240

Arg Asn Asp Leu Met Glu Leu Ile Gln Tyr Ala Pro Thr Thr Glu Thr
                245                 250                 255

Val Leu Lys Arg Pro Leu Leu Ile Val Pro Pro Trp Ile Asn Lys Phe
            260                 265                 270

Tyr Ile Leu Asp Leu Asn Pro Gln Lys Ser Leu Ile Gly Trp Met Val
        275                 280                 285

Ser Gln Gly Ile Thr Val Phe Val Ile Ser Trp Val Asn Pro Asp Glu
    290                 295                 300

Arg His Arg Asp Lys Asp Phe Glu Ser Tyr Met Arg Glu Gly Ile Glu
305                 310                 315                 320

Thr Ala Ile Asp Met Ile Gly Val Ala Thr Gly Glu Thr Asp Val Ala
                325                 330                 335

Ala Ala Gly Tyr Cys Val Gly Gly Thr Leu Leu Ala Val Thr Leu Ala
            340                 345                 350

Tyr Gln Ala Ala Thr Gly Asn Arg Arg Ile Lys Ser Ala Thr Phe Leu
        355                 360                 365

Thr Thr Gln Val Asp Phe Thr His Ala Gly Asp Leu Lys Val Phe Ala
370                 375                 380

Asp Glu Gly Gln Ile Lys Ala Ile Glu Glu Arg Met Ala Glu His Gly
385                 390                 395                 400

Tyr Leu Glu Gly Ala Arg Met Ala Asn Ala Phe Asn Met Leu Arg Pro
                405                 410                 415

Asn Asp Leu Ile Trp Ser Tyr Val Asn Asn Tyr Val Arg Gly Lys
                420                 425                 430

Ala Pro Ala Ala Phe Asp Leu Leu Tyr Trp Asn Ala Asp Ala Thr Arg
                435                 440                 445

Met Pro Ala Ala Asn His Ser Phe Tyr Leu Arg Asn Cys Tyr Leu Asn
        450                 455                 460

Asn Thr Leu Ala Lys Gly Gln Met Val Leu Gly Asn Val Arg Leu Asp
465                 470                 475                 480

Leu Lys Lys Val Lys Val Pro Val Phe Asn Leu Ala Thr Arg Glu Asp
                485                 490                 495

His Ile Ala Pro Ala Leu Ser Val Phe Glu Gly Ser Ala Lys Phe Gly
        500                 505                 510

Gly Lys Val Asp Tyr Val Leu Ala Gly Ser Gly His Ile Ala Gly Val
            515                 520                 525

Val Ala Pro Pro Gly Pro Lys Ala Lys Tyr Gly Phe Arg Thr Gly Gly
        530                 535                 540

Pro Ala Arg Gly Arg Phe Glu Asp Trp Val Ala Ala Thr Glu His
545                 550                 555                 560

Pro Gly Ser Trp Trp Pro Tyr Trp Tyr Lys Trp Leu Glu Glu Gln Ala
                565                 570                 575

Pro Glu Arg Val Pro Ala Arg Ile Pro Gly Thr Gly Ala Leu Pro Ser
            580                 585                 590

Leu Ala Pro Ala Pro Gly Thr Tyr Val Arg Met Lys Ala
        595                 600                 605

<210> SEQ ID NO 6
<211> LENGTH: 408
<212> TYPE: DNA
<213> ORGANISM: Sphingomonas elodea

<400> SEQUENCE: 6
tctagattcg atctcctcta ctggaattcg acgtcacca acctgccggc gacctggcac      60
ctcagctacc tgaccgacct ctaccgcgac aacaagctga tcgcgcccgg cgcgctcagc     120
atcggcggta ccccgatcga cctgtcgaag gtagaaacgc cgtcctatat ccaggccggg     180
cgcgaagatc acatcgcacc gccccgcagc gtctggaaga tgacggagca tttccgcggg     240
ccgcacaagt tcgtgctggc cggttccggc catatcgccg gcgtaatcaa tccgccttcg     300
gcaaagaaat accaatactg gaccaatgcc gggccggccg agtcgctcga atcctttgtc     360
gaaaacgcga cggaacatgc cggcagctgg tggcccccct ggactaga               408

<210> SEQ ID NO 7
<211> LENGTH: 1925
<212> TYPE: DNA
<213> ORGANISM: Sphingomonas elodea

<400> SEQUENCE: 7

```
ctgcaggaca tggccaaggg ccagatgacg cagaccgccg ccggcgcgtt cgagctcggc      60
cgcaacctgg cgatgacgcc gggcaaggtg gtgaagcgca cgccgctgta cgaactgatc     120
cagtattcgc cgacgacgga cacggtgctg gaaacgccgc tgatcatctt cccgccctgg     180
atcaaccgct tctacattct cgacctgacg ccggagaaga gcttcatccg ctgggcggtg     240
gcgcagggga tcaccgtgtt cgtcgtgtcg tggcgctcgg ccgatgcgag catgaaggac     300
gtggtgtggg acgattatgt cgagcgcggc cagatcgacg cgatcgacac cgtgcgcgag     360
ctgctcggcg tggaaagcgt ccacacgatc ggctattgcg tggcgggcac cacgctggcg     420
gcgacgctgg cggtgctcgc ggcgcgcggg gaggcggcga aggtggcgag cgcgaccttc     480
ttcaccgccc aggtcgactt caccgaggcg ggcgacctgc gcgtgttcgt cgacgacgac     540
cagctggcga tgatccgcag cctcggcgcc gacgggttcc tcgacgggcg ctacatggcg     600
gcgacgttca acctgctgcg cgggcgcgac ctgatctgga actacgtcac caacaactat     660
ctgatggggc aggaatatgc gccgttcgac ctgctccact ggaactcgga cgtcaccaac     720
ctgccggcgr cctggcacct cagctacctg accgacctct accgcgacaa caagctgatc     780
gcgcctctag acggcgcgct cagcatcggc ggtaccccga tcgacctgtc gaaggtagaa     840
acgccgtcct atatccaggc cggggcgcgaa gatcacatcg caccgccccg cagcgtctgg     900
aagatgacgg agcatttccg cgggccgcac aagttcgtgc tggccggttc cggccatatc     960
gccggcgtaa tcaatccgcc ttcggcaaag aaataccaat actggaccaa tgccgggccg    1020
gccgagtcgc tcgaatcctt tgtcgaaaac gcgacggaac atgccggaag ctggtggccg    1080
gactgggtgg actggttggt tgcgttgaac agtgcaaagg ttgcgacgaa aggtgcgcgg    1140
cttcccggca gtggaaacct ttgtgcaatc gccgacgcgc ccggcgaata tgttagaatg    1200
cgctgacggg aaggccgaat tttcgcgggt ttgacgattt ttgtgcactg cacaatggcg    1260
ccttgcaaaa tggccgtcga gcctttatat gttgcagcca gcaattggca gggaaagcta    1320
gtcacatggc cagcaaagga cctaagacga cggccaaacc ggcggcacgc ggtgctacca    1380
agcccgcgac tctggccgaa gctgccgcgg cgaagccgac gcctgcaccc gcccttgccg    1440
agacgatcgt cccggcagcg cgccggtgc cggcgcctgc cgaagccgct gcaccgcagg    1500
acgtgaagac caacatcgaa gaggcgatca ccgccccggt ggaaacggca gccgccgtca    1560
ccgagcaggc gatcgaagcc gcagagaccg tcgcgccggc ggtcaccacc agcaccgcga    1620
aggaaacgac tatcatggct accactttcg aaaacgcgac tacccaggcc cagaccgttt    1680
cgccgacct gaatgagcgc accaaggccg ccgtcgagaa gtcgaccaag ctggtcgagg    1740
aagccaacga gttcgccaag ggcaacatcg aagccctggt cgaatcgggc cgcatcgccg    1800
ccaagggctt cgagagcctg gccaggaag ctgccgatta cagccgccgc tcgttcgaga    1860
gcgcgaccgc cgcgctgaag ggcctgtcgt cggtcaagtc gccgaccgaa ttcttcaagc    1920
tgcag                                                                 1925
```

<210> SEQ ID NO 8
<211> LENGTH: 399
<212> TYPE: PRT
<213> ORGANISM: Sphingomonas elodea
<220> FEATURE:
<221> NAME/KEY: UNSURE
<222> LOCATION: (244)..(244)
<223> OTHER INFORMATION: Residue is either Thr or Ala.

<400> SEQUENCE: 8

Leu Gln Asp Met Ala Lys Gly Gln Met Thr Gln Thr Ala Ala Gly Ala

```
1               5                   10                  15
Phe Glu Leu Gly Arg Asn Leu Ala Met Thr Pro Gly Lys Val Val Lys
                20                  25                  30

Arg Thr Pro Leu Tyr Glu Leu Ile Gln Tyr Ser Pro Thr Asp Thr
            35                  40                  45

Val Leu Glu Thr Pro Leu Ile Ile Phe Pro Pro Trp Ile Asn Arg Phe
50                      55                  60

Tyr Ile Leu Asp Leu Thr Pro Glu Lys Ser Phe Ile Arg Trp Ala Val
65                  70                  75                  80

Ala Gln Gly Ile Thr Val Phe Val Val Ser Trp Arg Ser Ala Asp Ala
                85                  90                  95

Ser Met Lys Asp Val Val Trp Asp Asp Tyr Val Glu Arg Gly Gln Ile
            100                 105                 110

Asp Ala Ile Asp Thr Val Arg Glu Leu Leu Gly Val Glu Ser Val His
            115                 120                 125

Thr Ile Gly Tyr Cys Val Ala Gly Thr Thr Leu Ala Ala Thr Leu Ala
130                 135                 140

Val Leu Ala Ala Arg Gly Glu Ala Ala Lys Val Ala Ser Ala Thr Phe
145                 150                 155                 160

Phe Thr Ala Gln Val Asp Phe Thr Glu Ala Gly Asp Leu Arg Val Phe
                165                 170                 175

Val Asp Asp Asp Gln Leu Ala Met Ile Arg Ser Leu Gly Ala Asp Gly
            180                 185                 190

Phe Leu Asp Gly Arg Tyr Met Ala Ala Thr Phe Asn Leu Leu Arg Gly
            195                 200                 205

Arg Asp Leu Ile Trp Asn Tyr Val Thr Asn Asn Tyr Leu Met Gly Gln
            210                 215                 220

Glu Tyr Ala Pro Phe Asp Leu Leu His Trp Asn Ser Asp Val Thr Asn
225                 230                 235                 240

Leu Pro Ala Xaa Trp His Leu Ser Tyr Leu Thr Asp Leu Tyr Arg Asp
                245                 250                 255

Asn Lys Leu Ile Ala Pro Gly Ala Leu Ser Ile Gly Gly Thr Pro Ile
            260                 265                 270

Asp Leu Ser Lys Val Glu Thr Pro Ser Tyr Ile Gln Ala Gly Arg Glu
            275                 280                 285

Asp His Ile Ala Pro Pro Arg Ser Val Trp Lys Met Thr Glu His Phe
            290                 295                 300

Arg Gly Pro His Lys Phe Val Leu Ala Gly Ser Gly His Ile Ala Gly
305                 310                 315                 320

Val Ile Asn Pro Pro Ser Ala Lys Lys Tyr Gln Tyr Trp Thr Asn Ala
                325                 330                 335

Gly Pro Ala Glu Ser Leu Glu Ser Phe Val Asn Ala Thr Glu His
                340                 345                 350

Ala Gly Ser Trp Trp Pro Asp Trp Val Asp Trp Leu Val Ala Leu Asn
            355                 360                 365

Ser Ala Lys Val Ala Thr Lys Gly Ala Arg Leu Pro Gly Ser Gly Asn
            370                 375                 380

Leu Cys Ala Ile Ala Asp Ala Pro Gly Glu Tyr Val Arg Met Arg
385                 390                 395

<210> SEQ ID NO 9
<211> LENGTH: 28
<212> TYPE: DNA
<213> ORGANISM: Artificial Sequence
```

```
<220> FEATURE:
<221> NAME/KEY: primer_bind
<222> LOCATION: (1)..(28)
<223> OTHER INFORMATION: PCR primer PHADG5 to anneal with Sphingomonas
      elodea phaC gene fra

<400> SEQUENCE: 9
agtttctaga ttcgayctst aytggaay                                              28

<210> SEQ ID NO 10
<211> LENGTH: 31
<212> TYPE: DNA
<213> ORGANISM: Artificial Sequence
<220> FEATURE:
<221> NAME/KEY: primer_bind
<222> LOCATION: (1)..(31)
<223> OTHER INFORMATION: PCR primer PHADG7 to anneal with Sphingomonas
      elodea phaC gene fra

<400> SEQUENCE: 10
gtatactagt ccassssggc caccagctgc c                                          31

<210> SEQ ID NO 11
<211> LENGTH: 30
<212> TYPE: DNA
<213> ORGANISM: Artificial Sequence
<220> FEATURE:
<221> NAME/KEY: primer_bind
<222> LOCATION: (1)..(30)
<223> OTHER INFORMATION: PCR primer PHAC12 to anneal with Sphingomonas
      elodea to anneal wit

<400> SEQUENCE: 11
gttctctaga ggcgcgatca gcttgttgtc                                            30

<210> SEQ ID NO 12
<211> LENGTH: 31
<212> TYPE: DNA
<213> ORGANISM: Artificial Sequence
<220> FEATURE:
<221> NAME/KEY: primer_bind
<222> LOCATION: (1)..(31)
<223> OTHER INFORMATION: PCR primer PHAC11 to anneal with Sphingomonas
      elodea phaC gene fra

<400> SEQUENCE: 12
gttctctaga gagtcgctcg aatcctttgt c                                          31

<210> SEQ ID NO 13
<211> LENGTH: 3180
<212> TYPE: DNA
<213> ORGANISM: Sphingomonas ATCC 53159

<400> SEQUENCE: 13
gatccacacc ttgttctcgc gcgcccaggc gacgaggcgc tcgtagaagg cgaggtccac          60
cgtctccgcc gtcgggttcg acggatagtt gacgacgagg atcgacgggc gcggcacggt         120
gaagttcatt gcccgctcga ggctttcgaa ataggcgtcg tcgggcgtgg tcggcaccgc         180
gcggatcgtc gcgccggcga tgatgaagcc gaaggtgtgg atcgggtagc tggggttggg         240
cgcgagcacc acgtcgcccg gcgcggtgat cgcggtggcg aggctggcaa ggccctcctt         300
cgagcccatc gtgacgacga cctcggtctc gggatcgagc tcgacgccga atcggcggcc         360
ataataattg gcctgggcgc ggcgcaggcc cggaatgccc ttggactgcg aatagccgtg         420
cgcgtcgggc ttgcgcgcca cttcgcacag tttctcgatc acatggtcgg gcggcggcag         480
```

```
gtccggattg cccatgccga ggtcgataat gtcctctccg cccgcgcgtg ccgctgcccg      540
catcgcgttc acttcggcga tgacataggg aggcaagcgc ttgatgcggt agaattcttc      600
ggacatttcc tcgactttca agggttttga cacgcgacac aaaattgtgt cgtgcgcgcg      660
ttctacgcca taatcgcgca tccgggaatg acgcattgct ccgcctgcgc taagccgggg      720
cgaaggagag gaccgaatgg ccgatacgct cacgccgacc ctgccccgac tggaagacct      780
gcagcattgg acctgggtgc tgggccgcgc gcagcagatg atgctggagc atgggctgga      840
cctgatggag catgtgcccg ccgcgccccc cttcggcatg ctgctcgatc cgaccccggc      900
aatgcgggcg agcgcggacc tctgggcgga cacgatgcag ctgtggcagc gcttcctcga      960
tcccgcccat gccgagccgt tcgtcgaatc gcccgagcag gcgcgcgaca agcgcttcaa     1020
ggcgccgcaa tggcgcgagg agccggtgtt cgatttcctg cggcagagct atttcgtgat     1080
cgccgaccac atgctcaggc aggtcgaggc gctcgagcat gtcgacgagc ggcagcggga     1140
ccagatccgc ttcgccacca agggcttcat cgacgcgatc agccccacca acttccccgc     1200
caccaatccg caggtgatcg agaagatcgt cgagaccaag ggggaaagcc tgctcaaggg     1260
cctgcagcat atgctgcagg acatggccaa gggccagatg acgcagaccg ccgccggtgc     1320
gttcgagctc ggccgcaacc tggcgatgac gcccggcaag gtggtgaagc gcacccccgct    1380 ctacgaactg atccagtatt cgccgaccac cgagaccgtg ctggaaacgc cgctgatcat     1440
cttcccgccc tggatcaacc gcttctacat cctcgacctg acgcccgaga aaagcttcat     1500
ccgctgggcg gtggagcagg gatcaccgt gttcgtcgtc tcctggcgct cggccgatgc      1560
gagcatgaag gacgtggtgt gggacgatta tgtcgagcgc ggccagatcg acgcgatcga     1620
cacggtgcgc gcgctgctcg gcgtcgagag cgtccatacc atcggctatt gcgtggcggg     1680
caccacgctg gcggcgacgc tggcggtgct cgccgcgcgc gggcaggcgg cgaaggtggc     1740
gagcgcgacc ttcttcaccg cgcaggtcga tttcaccgag gcgggcgacc tgcgcgtgtt     1800
cgtcgatgac gaccagctgg cgatgatccg cagcctcagc gccgacggct tcctcgacgg     1860
gcgctacatg gcggcgacct tcaacctgct gcgcggccgc gacctgatct ggaactacgt     1920
caccaacaac tatctgatgg ggcaggaata tgcgccgttc gacctgctcc actggaactc     1980
ggacgtcacc aacctgccgg cgacctggca tctcagctac ctgaccgacc tgtaccgcga     2040
caacaagctg atcgcgcccg gcgcgctgcg catcggcggc accccggtcg acctttcgaa     2100
ggtcgaaacg ccgtcctaca tccaggccgg ccgcgaagat catatcgcgc cgccgcaaag     2160
cgtctggaag atcaccgagc atttccgcgg gccgcacaag ttcgtgctgg cgggttccgg     2220
gcatatcgca ggtgtaataa acccccggc ggcgaagaaa taccaatact ggaccaatac      2280
agggcctgcc gagtcgctcg actccttat cgaaaccgcg acggaacatg cgggaagttg      2340
gtggccggat tggctggatt gggtccgtgc gctgaacggt gcaaaggttg cgacgagcgg     2400
tgcgcgggtg ccgggggggtg gtaacctttg tgcagttgcg gaagcgcccg gcgactatgt     2460
tagaatgcgc tgacaaagag gcagaattc gtgggtttct ggcgttttg tgcactgcac      2520 aatgatcgct tgcaaaagca gcgccaagtc tttatatgct gcagtgcagc aatagccagg     2580
gaaagctagt cacatggcca gcaaaggacc caagacgacg ccaaacccg ccgcaaaatc      2640 agcggctcgc ggtgctatca agcccgcgat tctggccgaa gctgccgcgg cgacgccggc     2700
gtctgtacct cccgttgccg agacgatcgt cccggccgcg cgttggtgc ctgcgccgga      2760 cgaagccgct gcaacgcagg aagtgacgac tcacatcaaa gacacggtcg acgttgcggc     2820
ggaaacggta aaggccgtcg ccgaacacgc gatcgaagcc gcagagaccg tcgcgccggc     2880
```

```
ggtcaccacc agcaccgcga aggaaccgac tatcatggcc accactttcg agaacgcgac    2940
cacccaggcc cagactgttt tcgccgacct caacgagcgc accaaggccg ccgtcgaaaa    3000
gtcgaccaag ctggtcgagg aagccaacga gttcgccaag ggcaacatcg aggcgctggt    3060
cgaatccggc cgcatcgctg ccaagggctt cgagacgctg ggccaggaag ccgccgatta    3120
cagccgtcgc tcgttcgaga acgccacgac cacgctgaag agcctgtcgt cggtgaagtc    3180

<210> SEQ ID NO 14
<211> LENGTH: 32
<212> TYPE: DNA
<213> ORGANISM: Artificial Sequence
<220> FEATURE:
<221> NAME/KEY: primer_bind
<222> LOCATION: (1)..(32)
<223> OTHER INFORMATION: PCR primer 1Xba to anneal with Sphingomonas sp.
      ATCC 53159 gene fr

<400> SEQUENCE: 14
attctagaga tgatgaagcc gaaggtgtgg at                                  32

<210> SEQ ID NO 15
<211> LENGTH: 25
<212> TYPE: DNA
<213> ORGANISM: Artificial Sequence
<220> FEATURE:
<221> NAME/KEY: primer_bind
<222> LOCATION: (1)..(25)
<223> OTHER INFORMATION: PCR primer 4Xba to anneal with Sphingomonas sp.
      ATCC 53159 gene fr

<400> SEQUENCE: 15
attctagatg gtgcgctcgt tgagg                                          25

<210> SEQ ID NO 16
<211> LENGTH: 34
<212> TYPE: DNA
<213> ORGANISM: Sphingomonas sp. ATCC 531559

<400> SEQUENCE: 16
gaaattctgc ctctttgtcg gtcctctcct tcgc                                34
```